United States Patent
Raines

(10) Patent No.: US 10,894,166 B2
(45) Date of Patent: Jan. 19, 2021

(54) STIMULATION THERAPY LEAD TRIAL CABLE CONNECTOR

(71) Applicant: ADVANCED NEUROMODULATION SYSTEMS, INC., Plano, TX (US)

(72) Inventor: Aaron Raines, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 121 days.

(21) Appl. No.: 16/255,564

(22) Filed: Jan. 23, 2019

(65) Prior Publication Data

US 2020/0230425 A1 Jul. 23, 2020

(51) Int. Cl.
| | | |
|---|---|---|
| *A61N 1/00* | (2006.01) | |
| *A61N 1/375* | (2006.01) | |
| *A61N 1/04* | (2006.01) | |
| *A61N 1/36* | (2006.01) | |
| *A61N 1/372* | (2006.01) | |
| *A61N 1/378* | (2006.01) | |

(52) U.S. Cl.
CPC .......... *A61N 1/3754* (2013.01); *A61N 1/048* (2013.01); *A61N 1/36062* (2017.08); *A61N 1/36125* (2013.01); *A61N 1/3787* (2013.01); *A61N 1/37241* (2013.01); *A61N 1/36071* (2013.01)

(58) Field of Classification Search
CPC .............. A61N 1/3754; A61N 1/36014; A61N 1/36017; A61N 1/3752; A61N 1/36125; A61N 1/3787; A61N 1/048; A61N 1/36062; A61N 1/37241; A61N 1/36071
See application file for complete search history.

(56) References Cited

U.S. PATENT DOCUMENTS

| | | |
|---|---|---|
| 6,154,678 A | 11/2000 | Lauro |
| 6,415,168 B1 | 7/2002 | Putz |
| 7,548,788 B2 | 6/2009 | Chinn et al. |
| 9,054,436 B2 | 6/2015 | Swanson et al. |
| 9,827,424 B2 | 11/2017 | Kaula et al. |
| 9,844,661 B2 | 12/2017 | Franz et al. |
| 2014/0343564 A1 | 11/2014 | Feler et al. |
| 2017/0197079 A1* | 7/2017 | Illegems ............ A61N 1/37211 |
| 2018/0008821 A1 | 1/2018 | Gonzalez et al. |
| 2019/0366101 A1* | 12/2019 | Mcsherry ............ A61N 1/3752 |

FOREIGN PATENT DOCUMENTS

WO 2016/025909 A1 2/2016

* cited by examiner

*Primary Examiner* — Scott M. Getzow

(57) ABSTRACT

A multi-lead stimulation lead connector for facilitating electrical and mechanical connectivity between one or more stimulation leads and a pulse generator, e.g., an EPG used in a test stimulation system. One or more cam lock assemblies are disposed in a housing, each cam lock assembly comprising a cam knob and a cam shaft and having a longitudinal channel defined therein for accepting a proximal end of a respective stimulation lead, the proximal end having a plurality of terminal contact electrodes. By actuating a rotational movement of the cam knob, the cam lock assembly is unlocked in a first direction for guiding the proximal end and locked in a second direction for securely holding the proximal end and effectuating electrical connectivity with a plurality of conductors encapsulated in a cable for interfacing with the EPG.

18 Claims, 17 Drawing Sheets

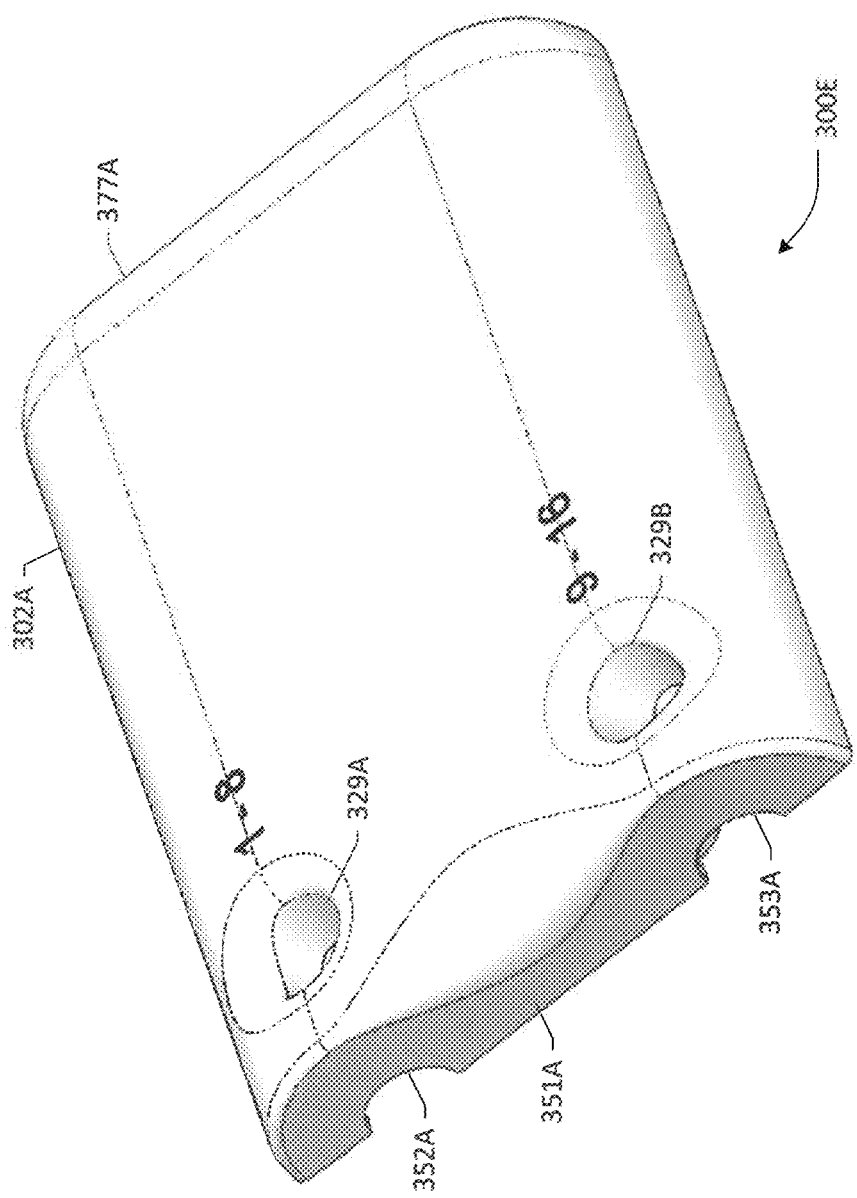

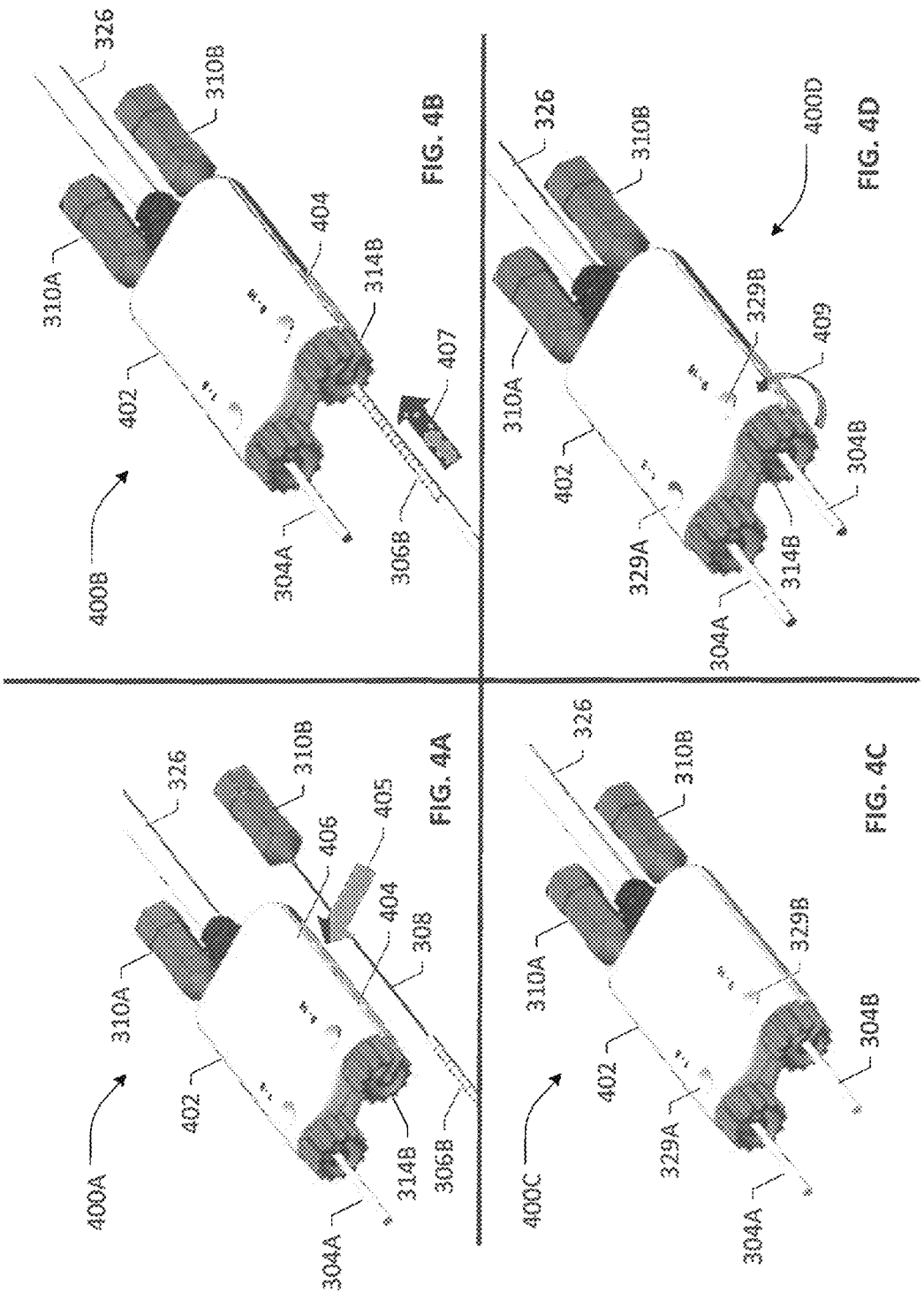

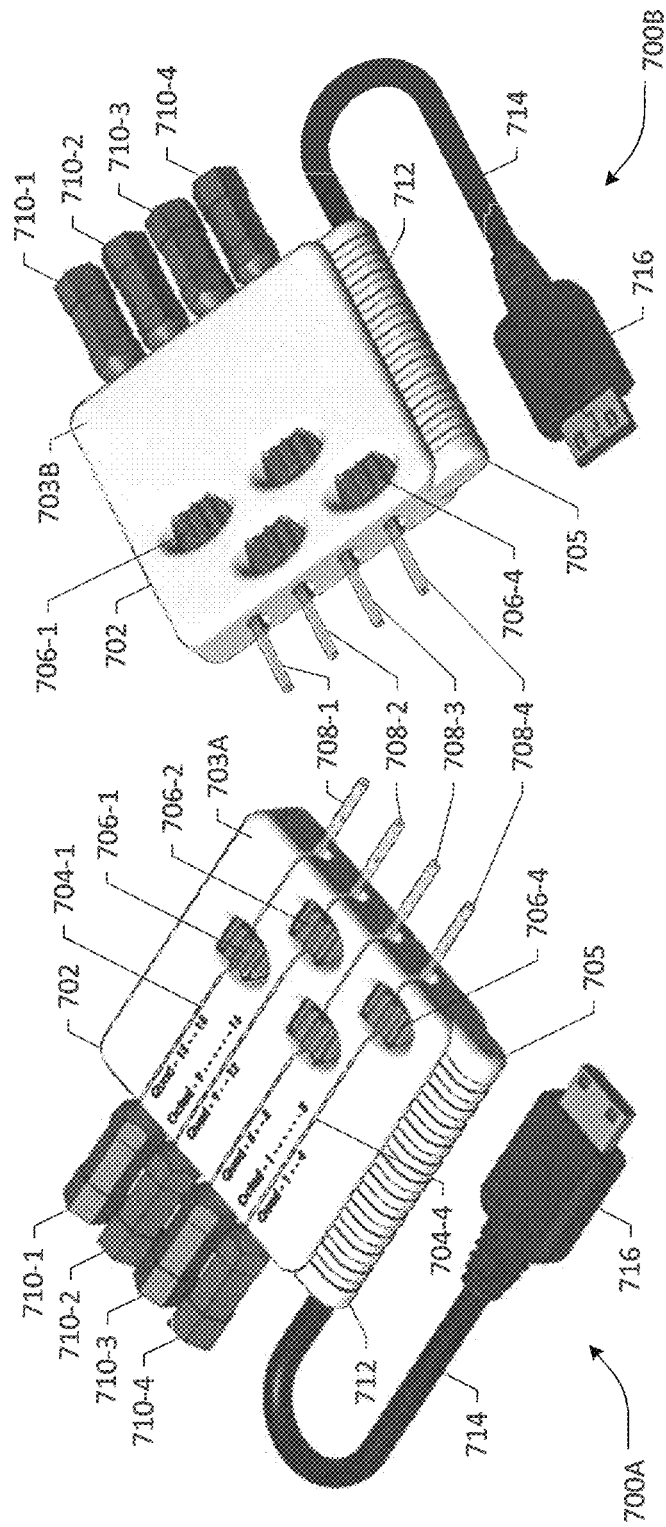

STIMULATION THERAPY LEAD TRIAL CABLE CONNECTOR

TECHNICAL FIELD

The present disclosure generally relates to stimulation therapy systems and lead connectors used in association therewith. More particularly, and not by way of any limitation, the present disclosure is directed to a multi-lead trial cable connector for facilitating electrical and mechanical connectivity with external pulse generators used in trial evaluation of neurostimulation systems (NS) including but not limited to spinal cord stimulation (SCS) systems.

BACKGROUND

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Stimulation systems may also be used in stimulating areas other than the spinal cord, such as for deep brain stimulation, muscle stimulation, etc.

Stimulation systems often comprise a pulse generator coupled to one or more therapy delivery leads having a plurality of electrodes disposed in an area in which neurostimulation is desired. Alternatively, stimulation systems may comprise a micro-stimulation system in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF)-based system. A typical IPG configuration comprises a surgically implanted, internally-powered pulse generator and one or more multi-electrode leads. A typical RF system configuration comprises a surgically implanted, passive receiver and a transmitter which is worn externally. In operation, the transmitter communicates, through an RF signal, to the implanted receiver to provide stimulation energy and control.

In an SCS application, electrodes used with an example pulse generator, such as any of the foregoing pulse generators, deliver a particularized electric field to a specific region of the spinal cord or surrounding tissue. Applying such an electric field across one or more nerve bundles and/or nerve roots, if properly directed and produced at the necessary levels, can "mask" certain forms of chronic pain in a phenomenon referred to as "paresthesia". Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation pulse amplitude, discharge method, and phase information, etc. (collectively referred to as "stimulation settings" or "stimsets").

Implantation of all or a portion of a stimulation system, e.g., a stimulation system including a fully implanted IPG or a RF system receiver/transmitter, necessarily requires a neurostimulation patient to undergo an implantation surgery. Additionally, routing a lead subdermally between an implanted pulse generator and the tissue area to be stimulated typically requires a relatively invasive procedure, such as a tunneling procedure. Likewise, explanting all or a portion of a stimulation system requires a neurostimulation patient to again undergo the trauma of surgery.

Chronically implantable electrical stimulation mechanisms have been the focus of advanced physiological engineering research for the past few decades. With the advent of microelectronics, it has become imperative to look into the criticality of safe functional electrical stimulation for large electrode arrays since stimulation electrode characteristics can change due to electrode dissolution/deterioration during prolonged use. Structural damage can occur if there is exposure to electrode potential much higher than applicable electrochemical windows associated with a tissue interface. Moreover, with large stimulation arrays employed in certain applications, monitoring the status of different electrodes becomes challenging.

Given the inherent risks involved in permanent implantation of a neurostimulation device into a patient, it is often desirable to evaluate a stimulation therapy on a trial basis by administering the intended therapy to the patient over a trial period in which an external pulse generator (EPG) is used to provide stimulation therapy via one or more implanted stimulation leads. During the trial phase, one or more leads are implanted temporarily, and a trial stimulator or EPG, connected to the implanted leads, may be programmed with one or more stimulation programs customized to the specific areas of the patient's pain. The trial phase, which typically takes several days, can be beneficial for a number of reasons. For instance, it can help the patient/physician analyze whether the intended therapy effectively achieves its objectives, e.g., relieve pain. The trial stimulation can also provide the patient/physician with an assessment period to determine which type of implantation lead technology works best. Additionally, it enables the patient/physician to evaluate different stimulation settings and programs, as well as help determine whether the patient's overall wellbeing is negatively impacted during the assessment period.

SUMMARY

It will therefore be appreciated that during a trial stimulation phase, one or more externalized stimulation leads are connected to a trial generator using a connection system. To help alleviate the discomfort experienced by the patient while undergoing the trial stimulation, a low profile multi-lead connector system is provided herein, which is particularly advantageous in applications involving multiple leads, where the existing connector technologies are often bulky and present numerous restrictions on the patient's day-to-day activities. It will be seen that example embodiments set forth in the present patent disclosure provide a trial cable connector solution where a balancing of mechanical forces is achieved in a suitable form factor such that while a stimulation lead is securely held without slippage (thereby ensuring proper electrical connectivity), it is configured in a manner in that the holding force is not so large that if a trial cable connecting the connector system to the external generator is accidently pulled, the stimulation lead would slip out of the cable connector and rather than from the patient.

Embodiments of the present patent disclosure are accordingly directed to a multi-lead cable connector for facilitating electrical and mechanical connectivity between one or more stimulation leads and a pulse generator, e.g., an external pulse generator (EPG) used in a test stimulation system, an external test evaluation (ETE) system, and the like, for evaluating a particular stimulation therapy application for a patient. In an exemplary embodiment, one or more cam lock assemblies are disposed in a housing, each cam lock assembly comprising a cam knob and a cam shaft and having a longitudinal channel defined therein for accepting a proximal end of a respective stimulation lead, the proximal end having a plurality of terminal contact electrodes. By actuating a rotational movement of the cam knob in a first direction (e.g., in a clockwise direction), the cam lock assembly may be unlocked and the proximal end of a stimulation lead may be guided into the longitudinal channel of the cam lock assembly using a stylet's guide wire. By actuating a rotational movement of the cam knob in a second direction (e.g., a counter-clockwise direction) opposite to the first direction, the cam lock assembly may be locked, whereupon the plurality of terminal contact electrodes of the proximal end are engaged to make contact with a plurality of conductive spring contacts disposed in the housing, which are connected to a plurality of conductors encapsulated in a cable for interfacing with the EPG.

In one aspect, an embodiment of the present disclosure is directed to a stimulation therapy lead connector configured to facilitate electrical and mechanical connectivity between at least one stimulation lead and an external pulse generator, the at least one stimulation lead having a distal end with a plurality of stimulation electrodes and a proximal end with a corresponding plurality of terminal contact electrodes, the proximal end having an outer diameter and an inner diameter, wherein the distal end of the at least one stimulation lead is implantable in a patient using a delivery tool's guide wire inserted into the at least one stimulation lead from the proximal end to guide the distal end to a target tissue area. The stimulation therapy lead connector comprises, inter alia, a housing; at least one cam lock assembly at least partially enclosed in the housing, the at least one cam lock assembly comprising a cam knob rigidly coupled to a cam shaft, the cam knob and the cam shaft having a longitudinal channel along a common axis, the longitudinal channel having at least a portion with a diameter sized to accommodate the outer diameter of the proximal end; a plurality of cantilevered conductive spring contacts mounted to a substrate securely disposed in the housing adjacent to the at least one cam lock assembly, the cantilevered conductive spring contacts operative to make electrical contact with the plurality of terminal contact electrodes of the proximal end after the proximal end is guided into the longitudinal channel using the guide wire inserted through a guide wire slot in the housing that is aligned with a longitudinal slit along the longitudinal channel when the cam knob is turned in a first direction and the at least one cam lock assembly is locked in a position by turning the cam knob in a second direction opposite to the first direction such that the longitudinal slit of the longitudinal channel is no longer aligned with the guide wire slot in the housing; and a plurality of conductors electrically connected to the plurality of cantilevered conductive spring contacts, the plurality of conductors encased in a cable having an interface for mating with an interface receptacle of the external pulse generator.

In another aspect, an embodiment of the present disclosure is directed to a trial stimulation therapy system operative to provide stimulation therapy to a patient for a trial period. The trial stimulation therapy system comprises, inter alia, an external pulse generator configured to provide stimulation therapy via a plurality of trial stimulation leads implanted into the patient at one or more target tissue areas; and a multi-lead stimulation lead connector interfaced with the external pulse generator via a cable and configured to facilitate electrical and mechanical connectivity between the plurality of trial stimulation leads and the external pulse generator. In one arrangement, the multi-lead stimulation lead connector comprises, inter alia: a housing; a plurality of cam lock assemblies at least partially enclosed in the housing, each cam lock assembly configured to connect to a corresponding trial stimulation lead, wherein each cam lock assembly comprises a cam shaft rigidly fixed to a cam knob that is rotationally turnable around a common axis of the cam knob assembly to a first position to unlock the cam lock assembly for facilitating insertion of a proximal end of the corresponding trial stimulation lead into a longitudinal channel defined in the cam shaft and to a second position to lock the cam lock assembly for presenting a plurality of terminal contact electrodes to a corresponding conductive spring contacts disposed in the housing; and a plurality of conductors electrically coupled to the plurality of conductive spring contacts, wherein the plurality of conductors are at least partially encased in the cable and extend to an interface operative for mating with an interface receptacle of the external pulse generator.

Additional/alternative features and variations of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 3E and 3F respectively depict exterior and interior views of a 3-dimensional perspective view of a top or upper housing portion of the example dual-lead connector shown in FIG. 3A;

FIGS. 4A-4D depict various steps of operating an example dual-lead connector for inserting and securing a trial stimulation lead using a cam lock assembly disposed therein according to an embodiment of the present disclosure;

FIGS. 7A and 7B depict 3-dimensional perspective views of a quad-lead connector using four cam lock assemblies operative to connect four trial stimulation leads according to an embodiment of the present disclosure.

DETAILED DESCRIPTION

Figure 1:
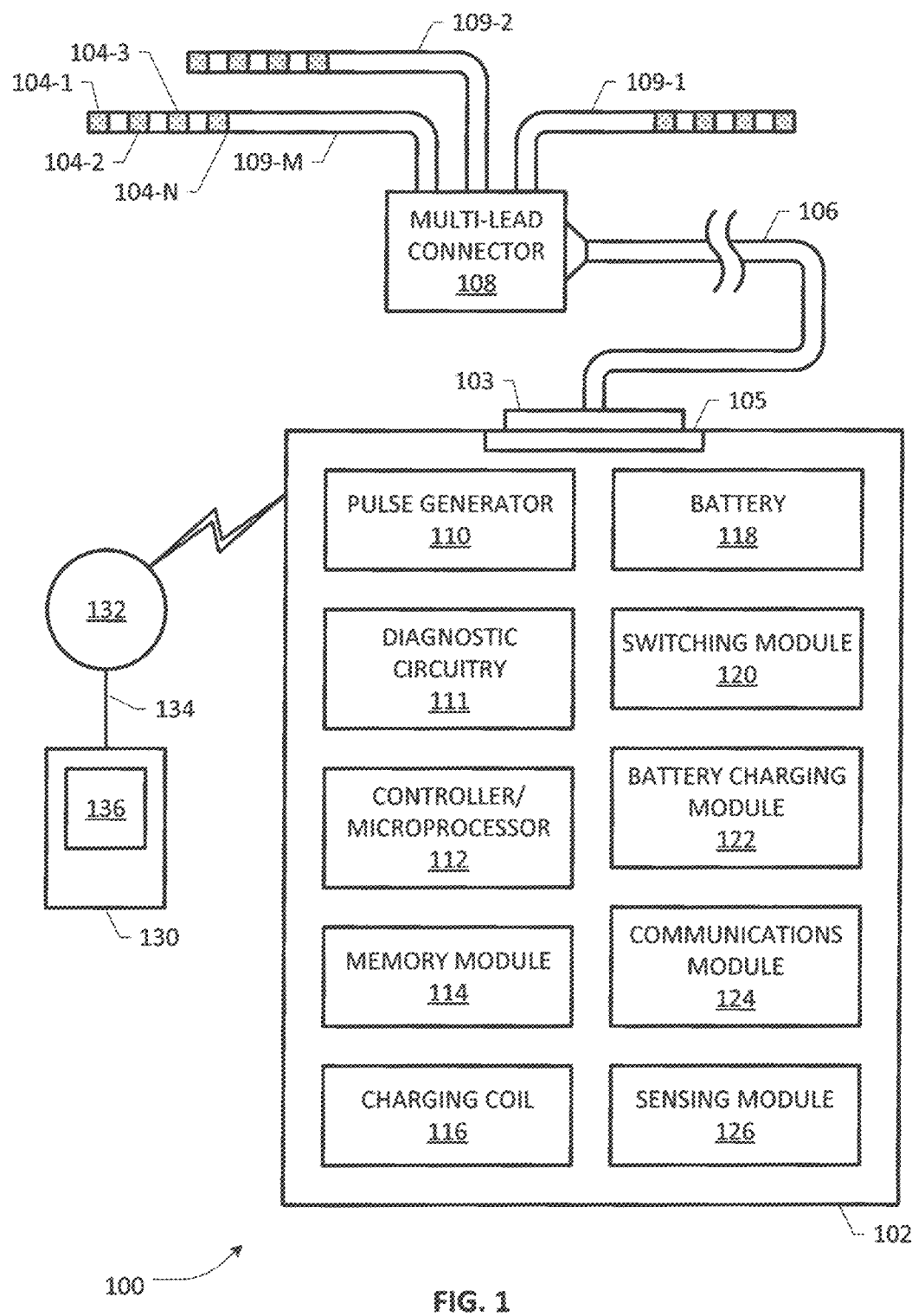
FIG. 1 depicts an example trial stimulation system wherein one or more embodiments of a multi-lead connector of the present disclosure may be practiced for effectuating electrical and mechanical connectivity between one or more trial stimulation leads and an external stimulator in an efficient form factor implementation according to the teachings herein.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth with respect to multi-lead connectors used in combination with an external pulse generator (EPG) for generating electrical stimulation in a trial period to a desired area of a body or tissue of a patient based on a suitable stimulation therapy application, such as a spinal cord stimulation (SCS) system. However, it should be understood that example multi-lead connectors and operation thereof disclosed herein are not limited thereto, but have broad applicability, including but not limited to different types of trial stimulation systems that may be used for other applications such as neuromuscular stimulators and sensors, dorsal root ganglion (DRG) stimulators, deep brain stimulators, cochlear stimulators, retinal implanters, muscle stimulators, tissue stimulators, cardiac stimulators, gastric stimulators, and the like, potentially including other bioelectrical sensors and sensing systems, which may be broadly referred to as "biostimulation" applications for purposes of the present disclosure. Moreover, example circuitry, methods of operation, and various types of multi-lead connectors disclosed herein are not limited to use with respect to an EPG or any particular form of EPG, or any particular type of trial stimulation leads. For example, some embodiments may be implemented with respect to an external trial evaluation of fully implantable pulse generators, radio frequency (RF) pulse generators, micro-implantable pulse generators, different types and configurations of electrodes, inter alia.

Referring now to the drawings wherein like or similar elements are designated with identical reference numerals throughout the several views, and wherein the various elements depicted are not necessarily drawn to scale, and referring to FIG. 1 in particular, depicted therein is an example trial stimulation system (TSS) or external trial evaluation (ETE) system 100 wherein one or more embodiments of a multi-lead connector of the present disclosure may be practiced for effectuating electrical and mechanical connectivity between one or more trial stimulation leads and an external stimulator in an efficient form factor implementation according to the teachings herein. By way of providing a generalized contextual application of a TSS or ETE system for evaluating a stimulation therapy, an overall description of system 100 is set forth immediately as follows. Broadly, system 100 may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 100 may typically include an external pulse generator (EPG) 102 that may be worn around a patient's waist, e.g., on a belt, or externally worn around or adjacent to any part of the patient's body depending on the therapy application (e.g., on the patient's back, around the patient's wrist, neck, shoulder, forearm, upper arm, thigh, leg, ankle, and the like), or in a pocket of an article of clothing, or in a separate wearable pouch, etc. In one example embodiment, EPG 102 may be implemented as having a housing formed of suitable biocompatible material that encloses a number of modules, e.g., a controller/processing block or module 112, pulse generating circuitry 110, a charging coil 116, a battery 118, a far-field and/or near field communication block or module 124, battery charging circuitry 122, switching circuitry 120, sensing circuitry 126, a memory module 114, and the like. It will be apparent to a skilled artisan that not all such functionalities may necessarily be included in a typical EPG implementation, however. In general, controller/processor module 112 typically includes a microcontroller or other suitable processor for controlling the various other components of the EPG device 102. Software/firmware code may be stored in memory 114 of EPG 102, which may be integrated with the controller/processor module 112, and/or other suitable application-specific storage components (not particularly shown in this FIG.) for execution by the microcontroller or processor 112 and/or other programmable logic blocks to control the various components of the device for purposes of a TSS/ETE application using an embodiment of the present patent disclosure.

In one arrangement, EPG 102 may be coupled to a multi-lead connector 108 according to an embodiment of the present disclosure, which may be advantageously configured for providing electrical and physical connectivity between EPG 102 and one or more implantable trial stimulation leads 109-1 to 109-M using a corresponding cam lock assembly mechanism for each trial lead as will be set forth in additional detail further below. Preferably, an embodiment of multi-lead connector 108 may be provided in a small, low profile form factor housing having one or more cam lock assemblies that are configured to receive corresponding stimulation leads 109-1 to 109-M at their respective proximal ends for securely engaging and providing electrical connectivity with respect to each stimulation lead's distal end having a plurality of stimulation electrodes. By way of illustration, trial stimulation lead 109-1 is exemplified with stimulation electrodes 104-1 to 104-N, which may be implanted near or adjacent to the patient's target tissue for a period of time with respect to evaluating a stimulation therapy before implementing a more permanent implantable pulse generator within the patient's body. Preferably, a single cable 106 is provided for electrically connecting the multi-lead connector 108 to EPG 102 via a suitable connector interface or socket 103 that may be mated to an interface receptacle or header portion 105 of EPG 102. In general, electrical pulses are generated by the pulse generating circuitry 110 under the control of processing block 112, and are provided to the switching circuitry 120 that is operative to selectively connect to electrical outputs of the EPG device 102, wherein one or more trial stimulation leads 109-1 to 109-M and/or one or more stimulation electrodes 104-1 to 104-N per each lead may be selectively configured, e.g., in different combinations, for providing appropriate stimulation pulses or therapy to different target tissues or regions or parts thereof depending on the stimulation protocols under evaluation. As will be set forth in detail below, respective electrical conductive traces corresponding to the one or more trial stimulation leads 109-1 to 109-M and/or one more stimulation electrodes 104-1 to 104-N per lead that are encapsulated in the cable 106 may be engaged in the multi-lead connector 108 using appropriate contact mechanisms provided in the multi-lead connector 108 upon locking the respective cam lock assemblies in the multi-lead connector 104 for electrically and mechanically engaging with corresponding terminal contact electrodes of the respective proximal ends of the stimulation leads 109-1 to 109-M during trial evaluation.

As different types of stimulation leads may be employed in an example trial stimulation evaluation system, a brief description thereof is set forth in the following sections. In one arrangement, stimulation electrodes 104-1 to 104-N of an example lead, e.g., lead 109-1, may be positioned along an axis of the lead 109-1, with an angular offset such that the lead electrodes 104-1 to 104-N do not overlap. The lead electrodes 104-1 to 104-N may be in the shape of a ring such that each lead electrode continuously covers the circumference of the exterior surface of the lead 109-1, which may comprise, e.g., an elongated, flexible tubular body. Typically, the lead electrodes 104-1 to 104-N are separated from each other by non-conducting portions of the lead 109-1, which electrically isolate each lead electrode 104-1 to 104-N from an adjacent lead electrode 104-1 to 104-N. The non-conducting portions of the lead 109-N may include one or more insulative materials and/or biocompatible materials to allow the lead 109-N to be implantable within the patient. Non-limiting examples of such materials include polyimide, polyether ether ketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally, or alternatively, stimulation lead electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N. Examples of such lead electrodes 104-1 to 104-N and associated fabrication processes are disclosed in one or more of the following: (i) U.S. Pat. No. 9,054,436, entitled, "METHOD OF FABRICATING STIMULATION LEAD FOR APPLYING ELECTRICAL STIMULATION TO TISSUE OF A PATIENT"; and (ii) U.S. Patent Application Publication No. 2018/0008821, entitled, "IMPLANTABLE THIN FILM DEVICES," each of which is incorporated herein by reference.

It should be noted the lead electrodes 104-1 to 104-N may also be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERYING THE SAME," which is incorporated herein by reference. Skilled artisans will, however, appreciate that providing percutaneous leads for trial stimulation may be more advantageous than paddle leads because of the less invasive surgical procedures required for the implantation of percutaneous leads.

In one arrangement, example trial stimulation leads 109-1 to 109-M may each comprise a lead body of insulative material encapsulating a plurality of conductors within the material that extend from a proximal end (that is proximate to the multi-lead connector 108) to the distal end of the lead body containing the stimulation electrodes 104-1 to 104-N. The conductors or conductive traces are operative to electrically couple the stimulation electrodes 104-1 to 104-N of example stimulation lead 109-1 to a corresponding plurality of terminals or terminal contact electrodes (not shown in FIG. 1) of the lead 109-1, which may be presented to respective contact points within the multi-lead connector 108 upon locking the corresponding cam lock assembly in an example embodiment as will be set forth further below in additional detail. By way of illustration, an example embodiment of the stimulation lead 109-1 may be provided with a plurality of lead electrodes 104-1 to 104-N comprising four electrodes, eight electrodes, etc., although any suitable number of electrodes (as well as corresponding conductive traces and terminals) may be provided in the trial stimulation system 100. Further, it should be appreciated that the trial stimulation leads 109-1 to 109-M may have different lengths and diameters/thicknesses, and may have the same or a different number of stimulation electrodes each. Correspondingly, the number of terminal contact electrodes of the stimulation leads 109-1 to 109-M may also be the same or different in an example implementation of the trial stimulation system 100. Additionally, or alternatively, one or more sensors (e.g., a position detector, temperature sensor, one or more electrochemical sensors, a radiopaque fiducial, etc.) may be located near the distal end of a trial stimulation lead, e.g., lead 109-1, and electrically coupled to terminals through associated conductors within the lead body.

Although not required for all embodiments, the lead body of an example trial stimulation lead 109-1 may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844,661, entitled "COMPLIANT ELECTRICAL STIMULATION LEADS AND METHODS OF FABRICATION," which is incorporated herein by reference.

With respect to providing various types of evaluative stimulation therapy using different stimulation leads for trial evaluation, one or more pulse generation circuitry blocks 110 may be employed, in combination with the switching module 120, to provide different stimulation pulses and waveforms including but not limited to high frequency pulse patterns (e.g., tonic stimulation waveform, burst stimulation waveform, and the like) as well as multi-stimset programs, as is known in the art. Various sets of parameters may define the pulse characteristics (e.g., constant voltage, constant current, etc.) and pulse timing for the pulses applied to the various leads and lead/electrode combinations as is also known in the art. In some embodiments, one or more additional external devices, e.g., device 130, may be implemented to interface with EPG 102 for various purposes. By way of illustration, an external device may be used for charging/recharging a battery 118 of EPG 102 (where provided), to access memory 114, and/or to program or reprogram EPG 102 with respect to the trial stimulation set parameters including pulsing specifications, stimsets, etc., while under evaluation for a particular patient. Accordingly, in some embodiments, one or more separate programmer devices may be employed for charging and/or programming the EPG 102 device and/or any programmable components thereof. An example embodiment of the additional external device 130 may be a processor-based system that possesses wireline and/or wireless communication capabilities, e.g., a tablet, smartphone, laptop computer, handheld computer, a personal digital assistant (PDA), or any smart wearable device and smart digital assistant device, etc, which may have one or more suitable user interfaces 136 (e.g., touch screen, keyboard, mouse, buttons, scroll wheels or rollers, voice input, or the like), allowing a user (e.g., a doctor, a medical technician, or the patient) to operate EPG 102. Software may be stored within a non-transitory memory of the external device 130, which may be executed by the processor to control the various operations of the external device 130. A connector or "wand" 134 may be electrically coupled to the external device 130 through suitable electrical connectors (not specifically shown), which may be electrically connected to a telemetry component 132 (e.g., RF transceiver, etc.) at the distal end of wand 134 through respective communication links that allow bi-directional communication with EPG 102.

In some embodiments, trial stimulation leads 109-1 to 109-M may be formed as implantable thin film devices, as previously noted. To manufacture an example implantable thin film device operative in an ETE arrangement, in one implementation, a shaped insulator, e.g., an elongated three-dimensional insulator formed as a tubular structure with a non-flat profile, with the insulator having an inner surface and an outer surface. may be formed from a substrate comprising one or more layers. The substrate may be made from an insulating material, including, without limitation, polyimide, organic thermoplastic polymer (e.g., polyether ether ketone (PEEK), liquid crystal polymer (LCP), flexible glass, flexible ceramic, rigid ceramic, and/or other insulating materials, as noted previously. The shaped insulator may be flexible, non-flexible (e.g., rigid), a combination of flexible and non-flexible, or transitionally stiff (e.g., transitioning or otherwise varying in stiffness from flexible to rigid along a length of the implantable thin film device or lead). The shaped insulator or substrate of an implantable thin film device, having an inner surface and an outer surface that extend along a length of the shaped insulator between a proximal end and a distal end, may be configured such that the outer surface at the distal end is arranged for contact with the tissue of a patient.

Once the shaped insulator is formed, a layer of conductive traces may be fabricated on the inner surface of the shaped insulator using biocompatible metallization, wherein the layer of conductive traces may be configured to define a trace pattern extending between the distal and proximal ends of the lead. In one implementation, the trace pattern may include one or more stimulation end traces, terminal end traces, and body traces. In one embodiment, the stimulation end traces may be fabricated on the inner surface of the shaped insulator at the distal end, the terminal end traces may be fabricated on the inner surface of the shaped insulator at the proximal end, and the body traces may connect the terminal end traces to the stimulation end traces. Such a trace pattern may be defined, for example, as a full tip-to-tail flexible circuit. In another implementation, the trace pattern may include stimulation end traces or terminal end traces configured to connect with a wound lead body. Such a trace pattern may be defined, for example, where the flexible circuit is a flexible circuit tip assembly. The trace pattern may further be defined depending on the selected TSS application involving, for example, different electrode counts and deployment methodologies, as known in the art. Further, the conductive trace pattern may include one or more sub-patterns and/or variations between the stimulation end and the terminal end, thereby providing additional flexibility to the flexible circuit as defined for the selected TSS application. For example, the trace pattern may include zig-zag patterns, linear patterns, angled patterns, contoured patterns, and/or the like. The trace pattern may vary along the stimulation end, the body, and the terminal end.

Figure 2A:
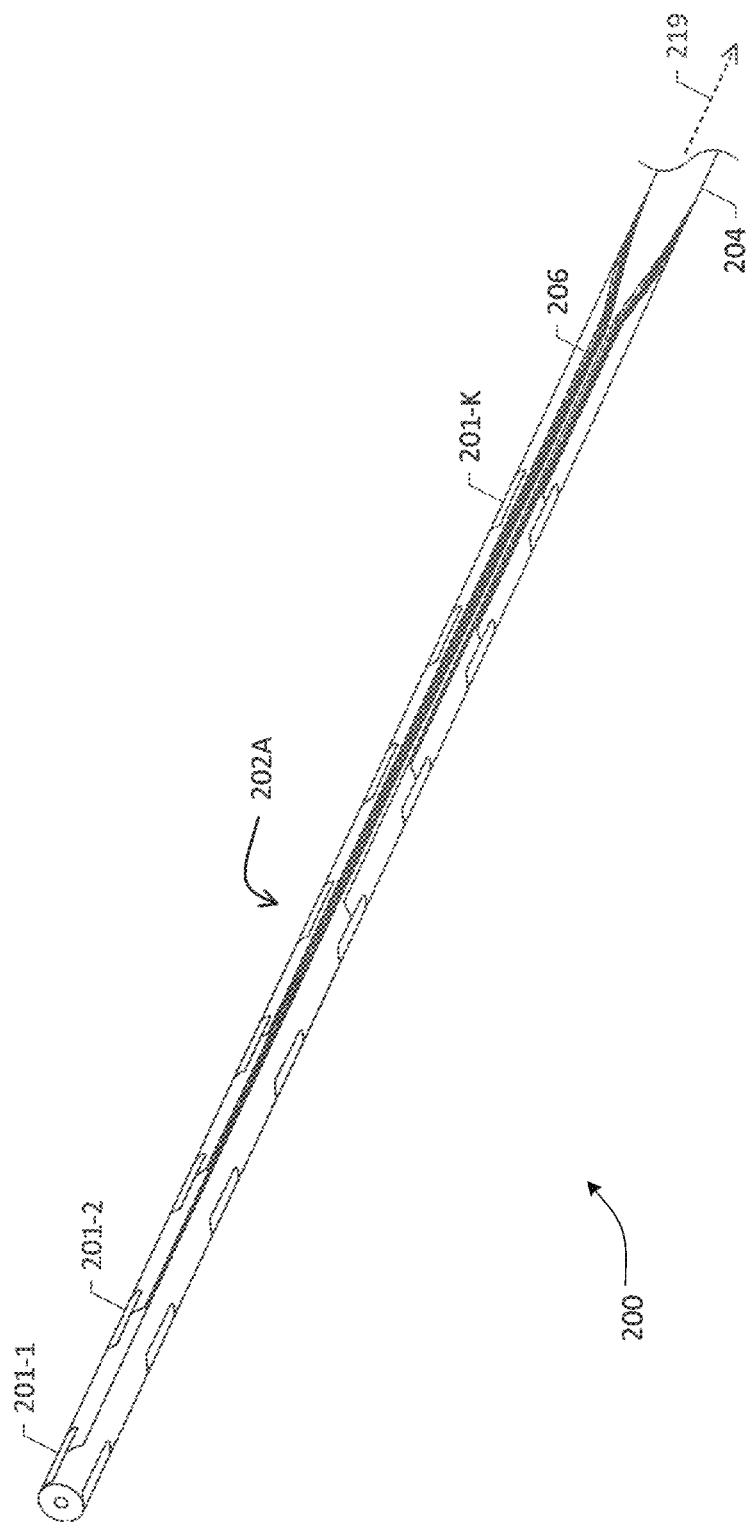
FIGS. 2A and 2B depict an example stimulation lead that may be used in association with a multi-lead connector according to an embodiment of the present disclosure.
Figure 2B:
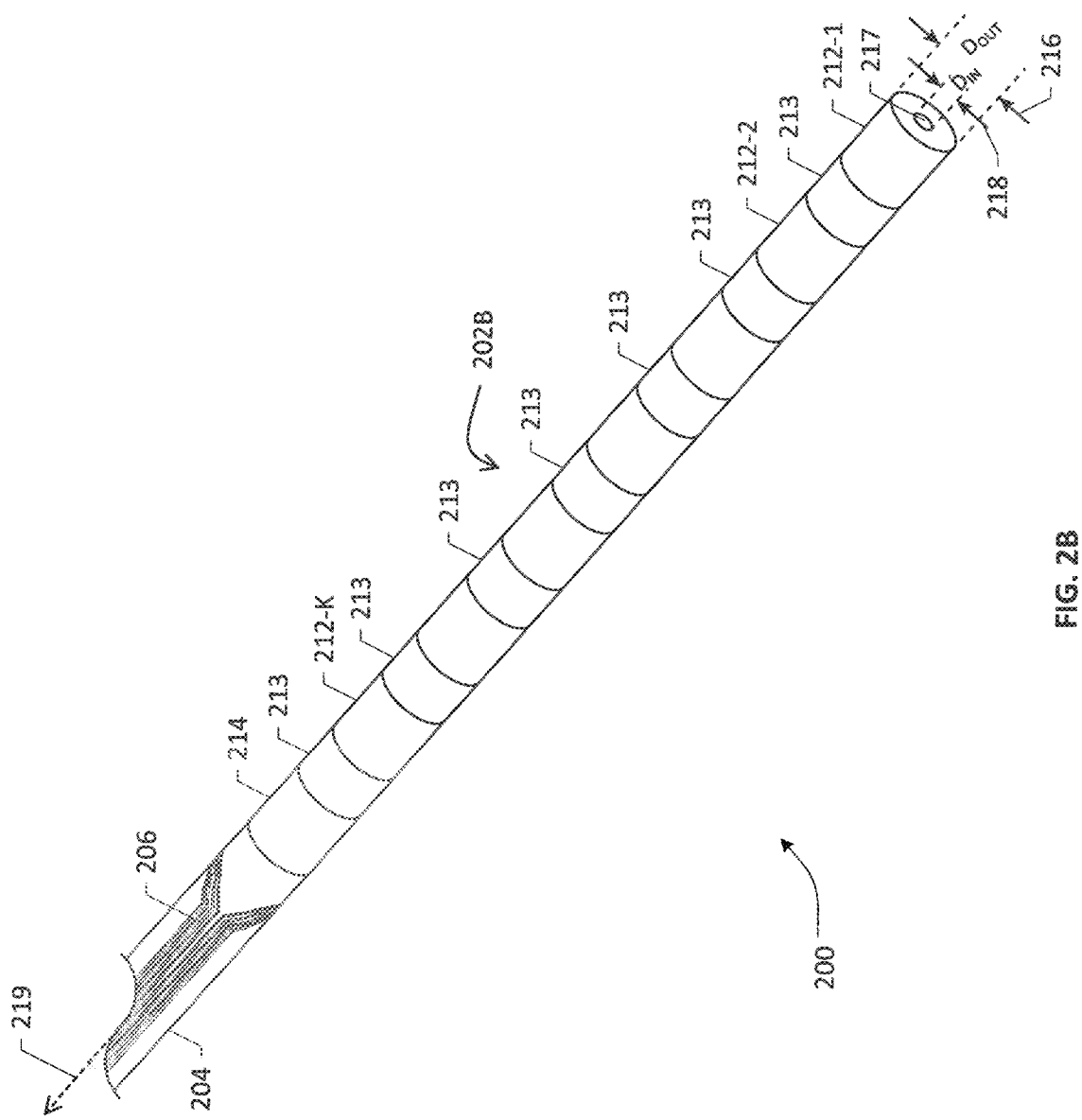

Turning to FIGS. 2A and 2B, depicted therein is an example stimulation lead 200 that may be used in association with a multi-lead connector of a TSS application according to an embodiment of the present disclosure. Reference numeral 202A shown in FIG. 2A refers to a distal end of the stimulation lead 200 having a plurality of stimulation electrodes 201-1 to 201-K, which are coupled to a corresponding plurality of conductors or conductive traces 206 that extend along a tubular body 204 toward a proximal end 202B shown in FIG. 2B. A plurality of terminal contact electrodes 212-1 to 212-K may be provided as ring electrodes at the proximal end 202B. In one implementation, the tubular stimulation lead 200 comprising distal end 202A, body 204 and proximal end 202B may be fabricated as a cylindrical thin film having a full tip-to-tail flexible circuit, as exemplified above, preferably operative to provide a K-channel trial stimulation per lead to a patient's target area.

As a cylindrical tubular structure, proximal end 202B of the lead 200 is illustrated as having an inner diameter $D_{IN}$ 218 defining a proximal orifice 217 and an outer diameter $D_{OUT}$ 216. Skilled artisans will recognize that in a percutaneous deployment into a target location of the patient, a stylet having a flexible wire (e.g., a guide wire), or similar delivery structure, having a suitable diameter that can be accommodated within the proximal orifice 217 may be inserted until the guide wire reaches the distal end 202A for implanting and guiding the distal end 202A to the target location. Additional details regarding an example deployment system for implanting a stimulation lead using a delivery tool such as a stylet having a guide wire may be found in the co-pending U.S. Patent Application Publication No. 2018/0008821, entitled, "IMPLANTABLE THIN FILM DEVICES," which is incorporated hereinabove by reference.

In one embodiment, terminal contact electrodes 212-1 to 212-K provided at the proximal end 202B are spatially separated by electrically non-conductive regions or rings 213 along the length of the proximal end 202B. Whereas a longitudinal dimension (i.e., a length) of each of terminal contact electrodes 212-1 to 212-K along a longitudinal axis 219 of the stimulation lead 200 may be configured to be the same in a preferred embodiment, some implementations may involve terminal contact electrodes 212-1 to 212-K having different sizes. In similar fashion, the interspersed insulator/non-conductive bands 213 separating adjacent terminal contact electrodes 212-1 to 212-K may have the same or different lengths along the longitudinal axis 219 of the stimulation lead 200. Further, in some embodiments, one or more insertion bands may be provided at the proximal end 202B, which are electrically inactive (i.e., not connected to any conductive traces operative to receive or provide stimulation pulses although fabricated using metallic or nonmetallic material) but essentially operate to provide a visual confirmation or indication that the proximal end is fully and completely engaged or otherwise aligned at a correct location or area in a receptacle configured to receive the proximal end. One skilled in the art will recognize that where multiple insertion bands are provided, they may comprise different sizes and may be interspersed in various ways among the terminal contact electrodes 212-1 to 212-K at selected locations along a length of the proximal end 202B. For example, where a pair of insertion bands are provided, a first insertion band may be located adjacent to a first terminal contact electrode 212-1 at the proximal orifice 217 and the other located adjacent to a last terminal contact electrode 212-K). By way of illustration, a single insertion band 214 provided adjacent to the terminal contact electrode 212-K is exemplified in the embodiment shown in FIG. 2B, which may be operative to provide a visual indication that the proximal end 202B is fully inserted or pressed against an abutment of a suitable receptacle where such full insertion is required for ensuring secure electrical and mechanical engagement.

In accordance with the teachings herein, one or more cam lock assemblies may be provided in a low profile multi-lead connector of the present disclosure (e.g., multi-lead connector 108 shown in FIG. 1) as an actuating or engaging mechanism for presenting and securely locking respective proximal end(s) of a corresponding number of stimulation leads, wherein suitable electrical connectivity is provided via a plurality of spring contacts housed in the multi-lead connector for each stimulation lead such that a single electrical cable may be provided for advantageously facilitating a common electrical interface with an EPG system. As will be set forth in further detail below, a cam lock assembly may be configured to accept the proximal end of a stimulation lead with a delivery deployment tool such as a stylet inserted in place, wherein various design considerations may closely follow the dimensions of a number of the features associated with the proximal end, e.g., inner and outer diameters of the proximal end, longitudinal length of the proximal end, insulator spacing between the terminal contact electrodes, the size of each terminal contact electrode as well as insertion bands (if/where provided), etc., as well as the dimensions relating to the delivery tool such as, e.g., the diameter or thickness of a stylet's guide wire, length of the exposed guide wire after it is fully inserted into a stimulation lead (e.g., the guide wire is pushed all the way through the body of the stimulation lead until it reaches a closed end of the distal end, which may typically be capped by a tip electrode), and the like. Furthermore, the operating principle of a cam lock assembly mechanism of the present disclosure is such that multiple cam lock assemblies may be accommodated together in a connector housing for facilitating a multi-lead configuration involving simultaneous but independent connections of multiple stimulation leads, e.g., a dual-lead configuration for connecting two stimulation leads, a quad-lead configuration for connecting up to four stimulation leads, etc. In the following sections, a cam lock assembly mechanism in an example dual-lead configuration is set forth with particular detail by way of illustration although the skilled artisans will recognize that the operating principle exemplified therein is equally applicable to other multi-lead configurations, e.g., a quad-lead configuration, mutatis mutandis.

Broadly, embodiments herein provide a cam lock assembly comprising a cam knob or head rigidly coupled to or integrally formed with a cam shaft having a longitudinal groove, channel or spacing along a common axis that is dimensioned to accept a proximal end of a trial stimulation lead, guided by a guide wire, wherein the action of rotating the cam knob in one direction locks and electrically contacts the terminal contact electrodes of the proximal end while rotating in the opposite direction unlocks and electrically disconnects the proximal end of the lead for easy removal. Depending on the number of the leads to be connected, a suitable connector housing may be provided for accommodating a corresponding number of cam lock assemblies, each with a cam knob for individually locking or unlocking a stimulation lead as needed.

Figure 3A:
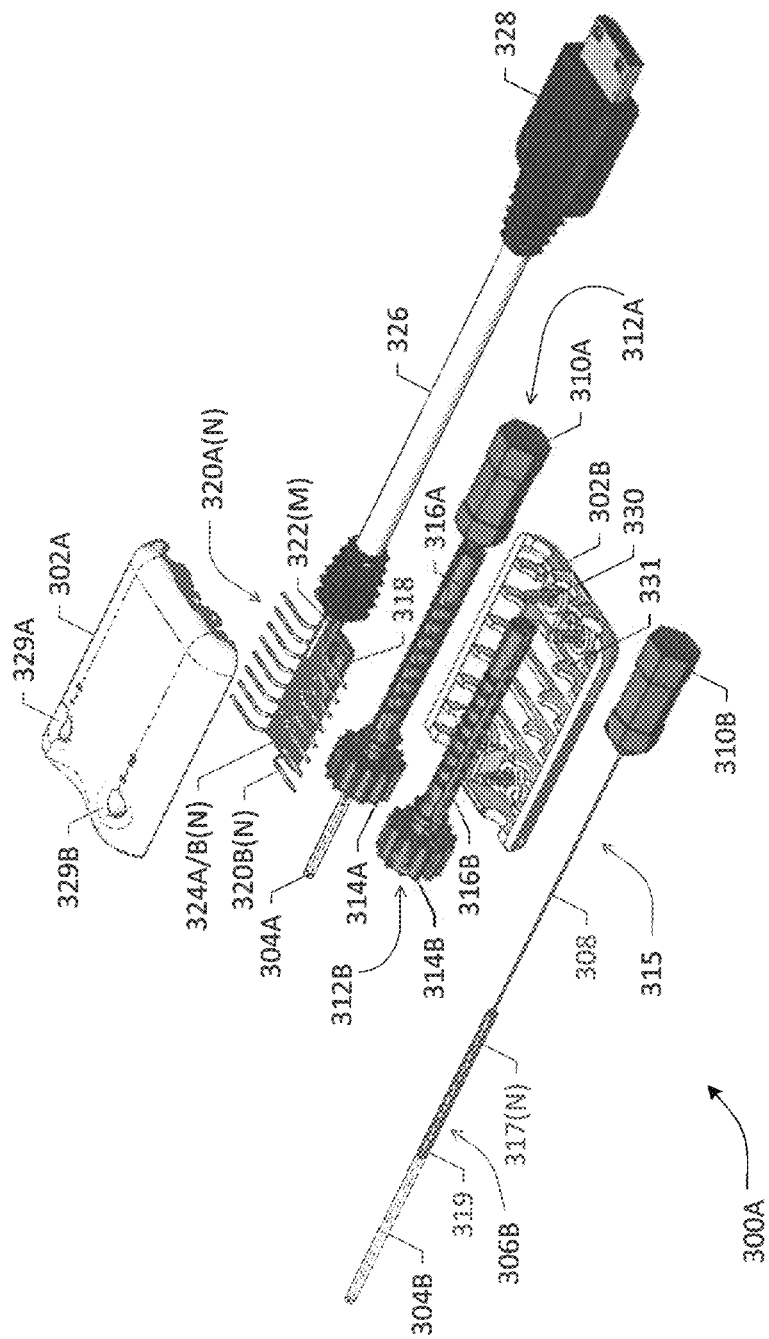
FIG. 3A depicts a 3-dimensional exploded view of an example dual-lead connector operative to connect two stimulation leads using respective cam lock assemblies according to an embodiment of the present disclosure.

Directing attention to FIG. 3A, depicted therein is a 3-dimensional exploded view of an example dual-lead connector 300A operative to connect two stimulation leads 304A/304B using respective cam lock assemblies 312A/312B according to an embodiment of the present disclosure. A housing comprising a upper housing portion 302A and a lower housing portion 302B may be formed, manufactured, assembled, or otherwise fabricated using any known or heretofore unknown technologies (e.g., injection molding, casting, 3D-printing, etc.,) involving suitable materials including but not limited to thermoplastic polymers, thermosetting polymers, elastomers, crystalline or non-crystalline amorphous solids, metals, and the like, such that the housing may be formed as a substantially rectangular 3-dimensional form having two guide wire slots formed on two longitudinal lateral sides, whose operation will be described in detail below. In one embodiment, the upper and lower housing portions 302A/302B may be rigidly coupled to each other using various coupling means such as, e.g., screws, bolts, rivets, binder posts, etc., wherein each housing portion may be provided with respective interior structural elements or members designed to facilitate the coupling of the two housing portions 302A/302B such as, e.g., screw posts 330 and corresponding screw holes (hidden from view in this FIG.). Further, the interior spaces of the upper and lower housing portions 302A/302B may also be provided with suitable structural elements or supporting members that may be contoured or otherwise formed to cooperatively define, when the two housing portions 302A/302B are mated together, two longitudinal spaces, cavities or recesses that are dimensioned to accommodate respective cam lock assemblies 312A/312B. In one embodiment, such interior supporting members may comprise an upper plurality of ribs, slats or transverse members (hidden from view in this FIG.) and a lower plurality of ribs, transverse members or slats 331, at least a respective portion of them having respective semi-circular cutouts, that may be mated to define the contours of a cavity, as will be further described below. Cam lock assemblies 312A, 312B are shown with respective cam knobs 314A, 314B, each coupled to or integrally formed with corresponding cam shafts 316A, 3168 that define and/or contain various additional features for receiving and engaging the proximal leads of respective stimulation leads as will be further described below. With respect to the example dual-lead connector 300A shown in the exploded view of FIG. 3A, stimulation lead 304A is illustrated as being fully inserted into the corresponding cam lock assembly 312A whereas stimulation lead 304B is shown prior to being inserted into the corresponding cam lock assembly 312B. As exemplified in FIG. 3A, a proximal end 306B of stimulation lead 304B is provided with a plurality of terminal contact electrodes 317(N) as well as an insertion band 319, similar to the stimulation lead embodiment 200 shown in FIGS. 2A/2B above. A delivery tool or stylet 315 comprising a handle 310B coupled to guide wire 308 is illustratively engaged with the stimulation lead 304B such that the guide wire 308 is inserted into the proximal end 306B thereof. On the other hand, because the proximal end of stimulation lead 304A is already inserted and engaged within the corresponding cam lock assembly 312A, only handle 310A of the corresponding delivery tool is shown in FIG. 3A. As will be described in further detail below, the guide wire slots formed on the lateral sides of the connector housing are dimensioned such that a guide wire portion of the delivery tool may be presented when the cam lock assembly is in an unlocked position for facilitating the insertion of the proximal end of a stimulation lead. With respect to facilitating electrical connectivity and mechanical engagement of the terminal contact electrodes of each stimulation lead 304A/304B, a substrate 318 having a plurality of contacts that are aligned lengthwise into two columns is positioned on a flat plane defined by the plurality of ribs 331 of the lower housing portion 302B. By way example, substrate 318 may be formed as a small printed circuit board (PCB) wherein the two rows of contacts are longitudinally aligned and further wherein each row of contacts is electrically connected with a corresponding set of cantilevered conductive spring contact members that are spaced apart, which can be pushed against a corresponding set of the plurality of terminal contact electrodes of a proximal end when it is fully inserted into the corresponding cam lock assembly and the cam knob portion thereof is rotated into a locking position. By way of illustration, the plurality of spring contact members 320A(N) are exemplified with respect to engaging the inserted proximal end of example stimulation lead 304A, wherein reference numeral 324A(N) refers to a corresponding plurality of substrate contacts provided on, in or through substrate 318. In one example embodiment, the plurality of spring contact members 320A(N) may be pivotally coupled to the corresponding plurality of substrate contacts 324A(N) for providing a right amount of tension that can provide secure mechanical engagement (e.g., to prevent accidental disconnecting of the lead due to snagging of the leads while the patient is asleep or resting, or when the patient is moving or engaged in some activity, etc., while still allowing easy removal of the lead by pulling without using an inordinate amount of force). Accordingly, in some embodiments, appropriate materials may be selected and shaped for operating as the conductive spring contacts and coupled to the substrate contacts in order to provide suitable electrical connectivity (e.g., soldering, brazing, etc.) while ensuring that certain mechanical constraints are also met depending on the particular TSS/ETE application. Substrate 318 may also be provided with well-known structures such as plate-through vias, conductive traces and pads, and the like for facilitating respective electrical connections between the spring contacts 320A(N)/320B(N) and corresponding wires or conductors, e.g., conductors 322(M), that may be encased or sheathed in a cable 326 having an interface 328 for mating with an interface receptacle or socket of an EPG (e.g., EPG 102 shown in FIG. 1). A skilled artisan will readily recognize that a variety of cabling options, form factors, and electro-mechanical interface options in myriad combinations may be implemented in an example implementation, e.g., such as ribbon cables, round cables, USB interfaces, multi-pin connectors, plugs or jacks, male-ended or female-ended connectors, and the like.

Where an example implementation involves the engagement of stimulation leads having respective insertion bands, the upper housing portion 302A may be provided with a pair of apertures or "view ports" 329A/329B disposed toward a lead-side wall of the housing, with each aperture aligned with the common axis of the respective cam assembly 312A/312B such that the aperture is positioned to line up with the location of the insertion band of the corresponding proximal end when the cam knob of a respective cam lock assembly is turned to a locking position with the proximal end fully inserted into the channel defined in the cam lock assembly. Each aperture 329A/329B may be suitably sized, e.g., based on the size or dimension of the corresponding insertion band, to provide a visual indication of the insertion band to indicate that the proximal end is fully inserted and locked into the respective cam lock assembly.

Figure 3B:
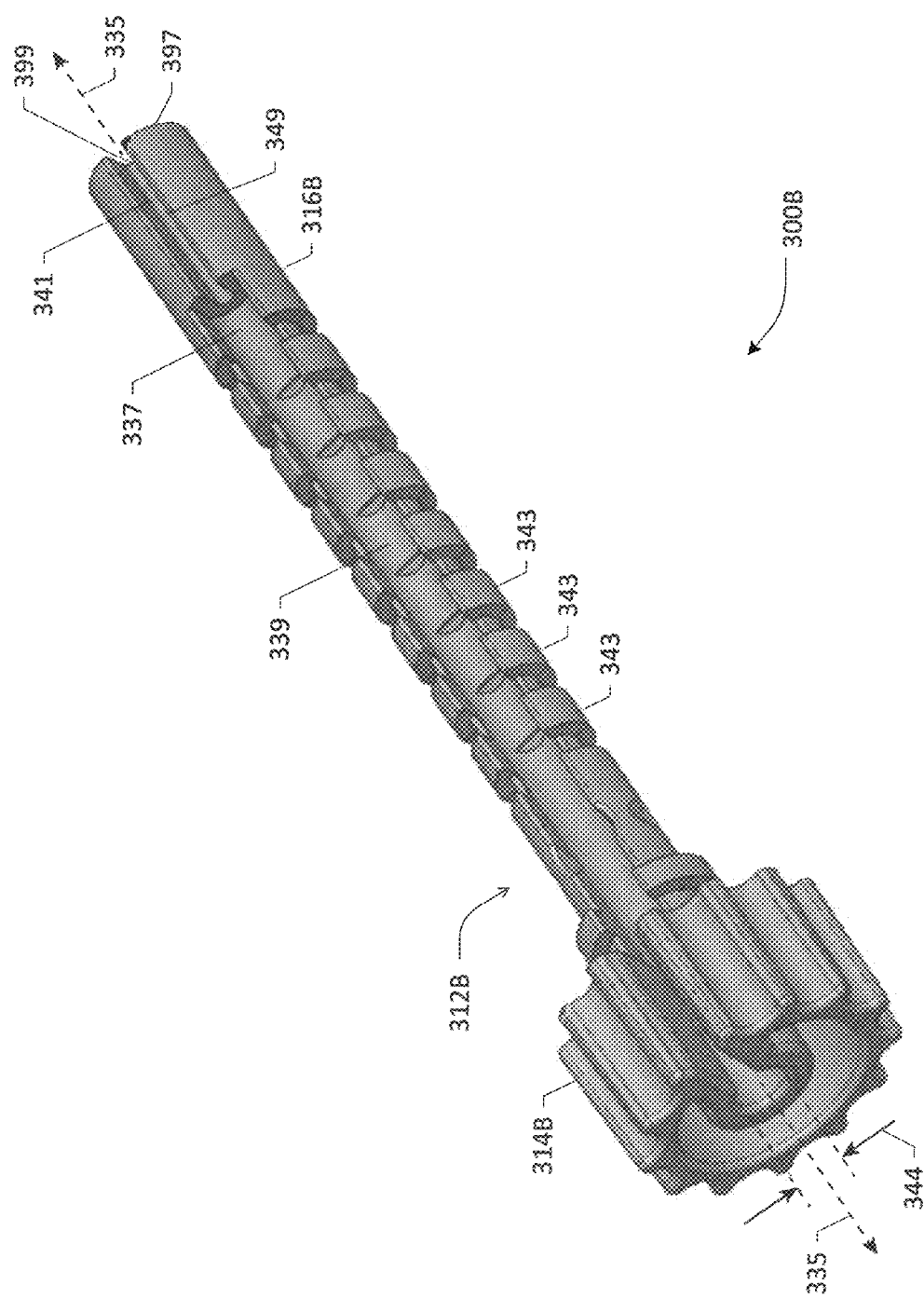
FIGS. 3B-3D depict various 3-dimensional perspective views of an example cam lock assembly for use with a multi-lead connector according to an embodiment of the present disclosure.
Figure 3C:
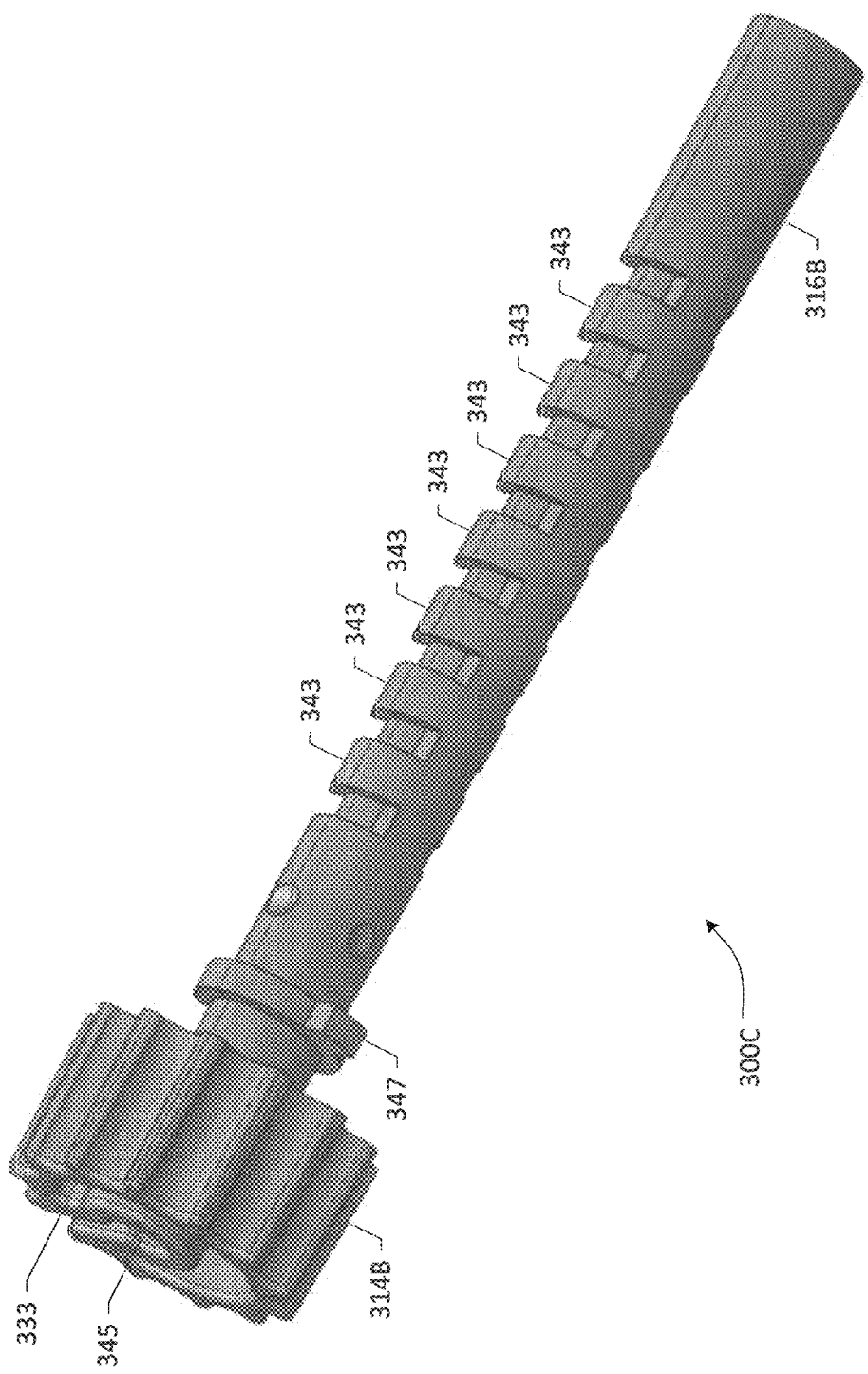
Figure 3D:
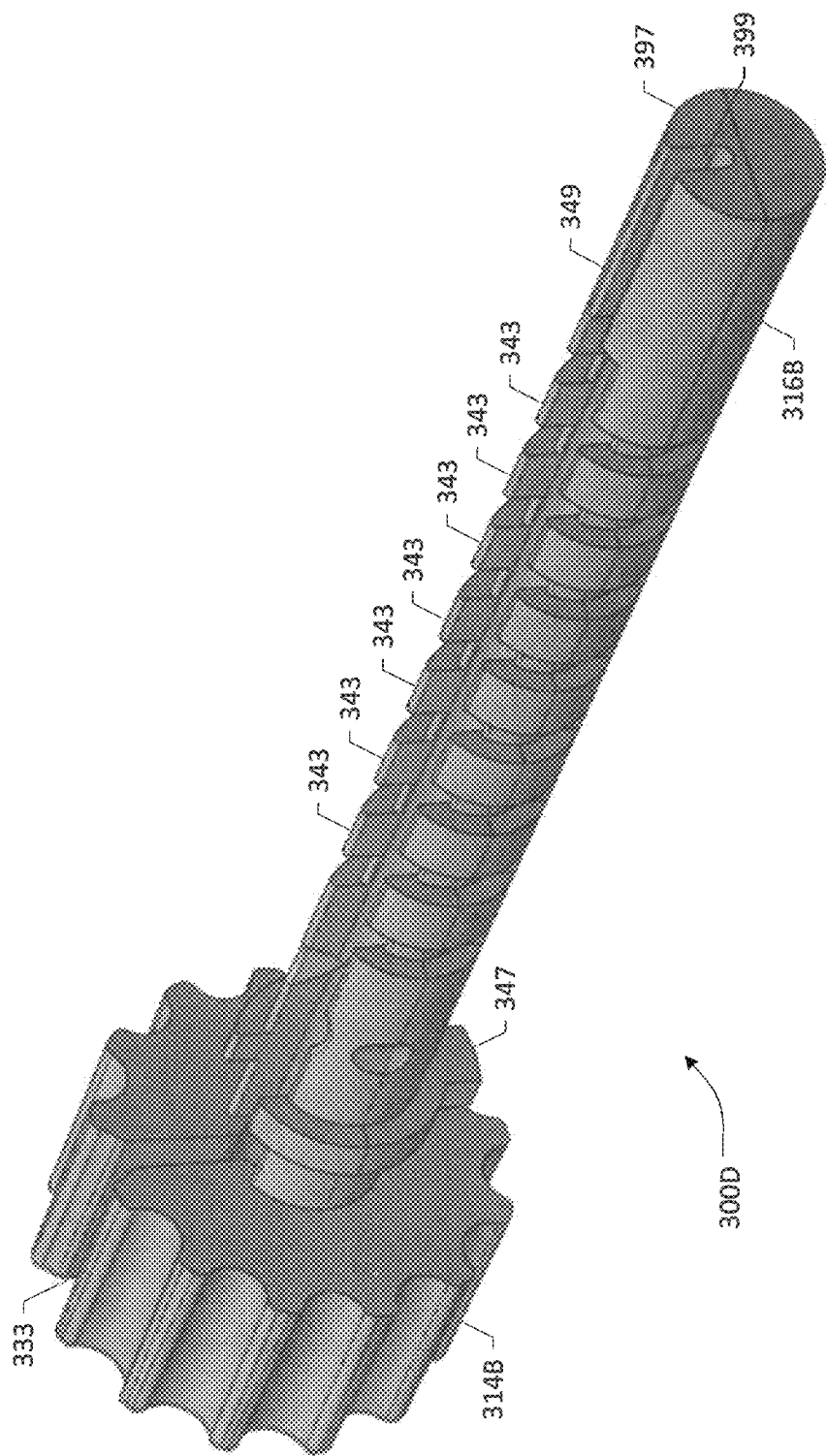

FIGS. 3B-3D depict various 3-dimensional perspective views of an example cam lock assembly for use with a multi-lead connector according to an embodiment of the present disclosure. By way of illustration, cam lock assembly 312B of FIG. 3A is exemplified in multiple views 300B-300D. Taking reference to FIGS. 3B-3D together, additional details of an example embodiment of cam lock assembly 312B may be set forth as follows. Preferably, cam knob or head 314B may be provided as a ridged or knurled structure having a substantially regular shape (e.g., a circle, square, pentagon, hexagon, octagon, etc.), wherein an aperture or orifice 345 with a diameter 344 is provided that opens into a longitudinal channel 337 defined along cam shaft or body 316B along a common axis 335. Preferably, the longitudinal channel 337 has a wider diameter portion 339 that extends into a narrow diameter portion 341 toward a terminus or end 339 of the cam shaft 316B. The narrow diameter portion 341 extends through terminus 339 of the cam shaft 316B, thereby creating a shaft terminus orifice 399 thereat. In one arrangement, the wider diameter portion 339 may comprise a diameter that is substantially same as the diameter 344 of the knob orifice 345, which is sized to accommodate an outer diameter of the proximal end of a stimulation lead (e.g., $D_{OUT}$ 216 of the proximal end 202B of lead 200 shown in FIGS. 2A/2B). It should be appreciated that the longitudinal channel 337 does not form a fully radially enclosed tubular space around the common axis 335. Rather, the longitudinal channel 337 is provided with a thin longitudinal slit or opening 349 along the common axis 335 which is preferably dimensioned to accommodate the diameter of a delivery tool's guide wire but not the proximal end when the proximal end is guided and fully inserted into the longitudinal channel 337 through the knob orifice 345. As illustrated, the longitudinal slit 349 comprises at least a portion through the cam knob 314A in the form of a groove 333 therein, which extends to an opening in the cam shaft 316A. Accordingly, referring back to FIG. 3A, when the proximal end 306B of stimulation lead 304B is inserted with the guide wire 308 of corresponding delivery tool 315 (e.g., by pushing the guide wire 308 at least partly or all the way toward and into the distal end of lead 304B until its inward movement is arrested at the distal end of lead 304B), whereby an exposed portion of the guide wire 308 may be slid into or through the longitudinal slit 349 for facilitating the insertion of the proximal end 306B through the knob orifice 345, the proximal end 306B may be pushed or guided into the wider diameter portion 339 of the longitudinal channel 337 until proximal end 306B buts up against the narrow diameter portion 341 toward the cam shaft terminus 339. Because the longitudinal slit 349 is narrower than the outer diameter of the proximal end 306B, the proximal end 306B held securely in place within the wider diameter portion 339 of the longitudinal channel 337 while fully inserted, with the guide wire 308 still place emerging from the terminus orifice 343 provided at terminus 399 of the cam shaft 316B.

To facilitate the presentation of a stimulation lead's proximal end into a cam lock assembly that is securely disposed in the connector housing, a guide wire slot may be provided in the housing that is also sized to accommodate only the guide wire but not the proximal end of the stimulation lead. As noted previously, such guide wire slots may be formed along on the longitudinal lateral sides of a dual-lead connector that are formed when the upper and lower housing portions 302A/302B are mated together and longitudinal seams are formed where the two portions are joined, which may be achieved in a streamlined fabrication process that is relatively cost-effective. Accordingly, it will be appreciated that an unlock position of a cam lock assembly mechanism for facilitating the insertion of a stimulation lead's proximal end involves aligning the longitudinal slit of the cam lock assembly with the longitudinal guide wire slot in the housing by turning, rotating or otherwise actuating the cam knob 314B in a first direction, e.g., clock-wise or counter-clockwise). Turning the cam knob 314B in an opposite direction (i.e., a second direction) rotates the cam shaft 316B with the proximal end securely disposed in the wider diameter portion 339 of the longitudinal channel 337 of the cam lock assembly (i.e., in a locking position), whereby the longitudinal slit of the cam lock assembly is no longer aligned with the guide wire slot in the housing.

The angle of knob rotation for locking and unlocking a cam lock assembly may be set so as to facilitate an optimal presentation of the plurality of terminal contact electrodes to the corresponding cantilevered conductive spring contacts while providing as much angular separation from a position where the longitudinal slit is perfectly aligned with the guide wire slot in the housing (i.e., in the unlocked state). Based on electromechanical design considerations, it can be seen that a 90° angular separation (i.e., a quarter-turn) is generally most optimal for fully exposing and presenting the terminal contact electrodes to the respective conductive spring contacts. Because of the cantilevered design employed in a presently preferred exemplary embodiment, the contact springs may be activated to exert optimal contact force on the respective terminal contact electrodes while still allowing a relatively small pull force for easy lead removal.

In one example embodiment, a plurality of substantially circular ridges, bumps or serrations 343 may be provided along an outer surface of the cam shaft 316B, which may be numbered and dimensioned based on the number and size of the terminal contact electrodes of a stimulation lead. Skilled artisans will recognize that such an arrangement is particularly advantageous in help preventing side-wise movement of the cantilevered conductive spring contacts (i.e., along the length of the cam shaft 316B) when the cam lock assembly is locked by appropriately turning the cam knob 314B, and hence the cam shaft 316B, whereupon the cantilevered conductive spring contacts are firmly engaged on respective terminal contact electrodes.

In a further embodiment, an outer or exterior surface of the cam shaft 316B may be provided with a projection or tab 347 operative to mechanically restrict a rotational movement of the cam knob 314B around the common axis to only a quarter turn from a first position when the cam lock assembly 312B is unlocked (i.e., the longitudinal slit along the longitudinal channel of the cam lock assembly is aligned to the guide wire slot in the housing) to a second position when the cam lock assembly 312B is locked such that the longitudinal slit of the longitudinal channel is no longer aligned with the guide wire slot in the housing and the terminal contact electrodes are in secure engagement, electrically and mechanically, with the corresponding plurality of cantilevered spring contacts disposed in the housing. Additional details and/or further variations with respect to locking and unlocking operations of an example cam lock assembly will be set forth further below.

Figure 3F:
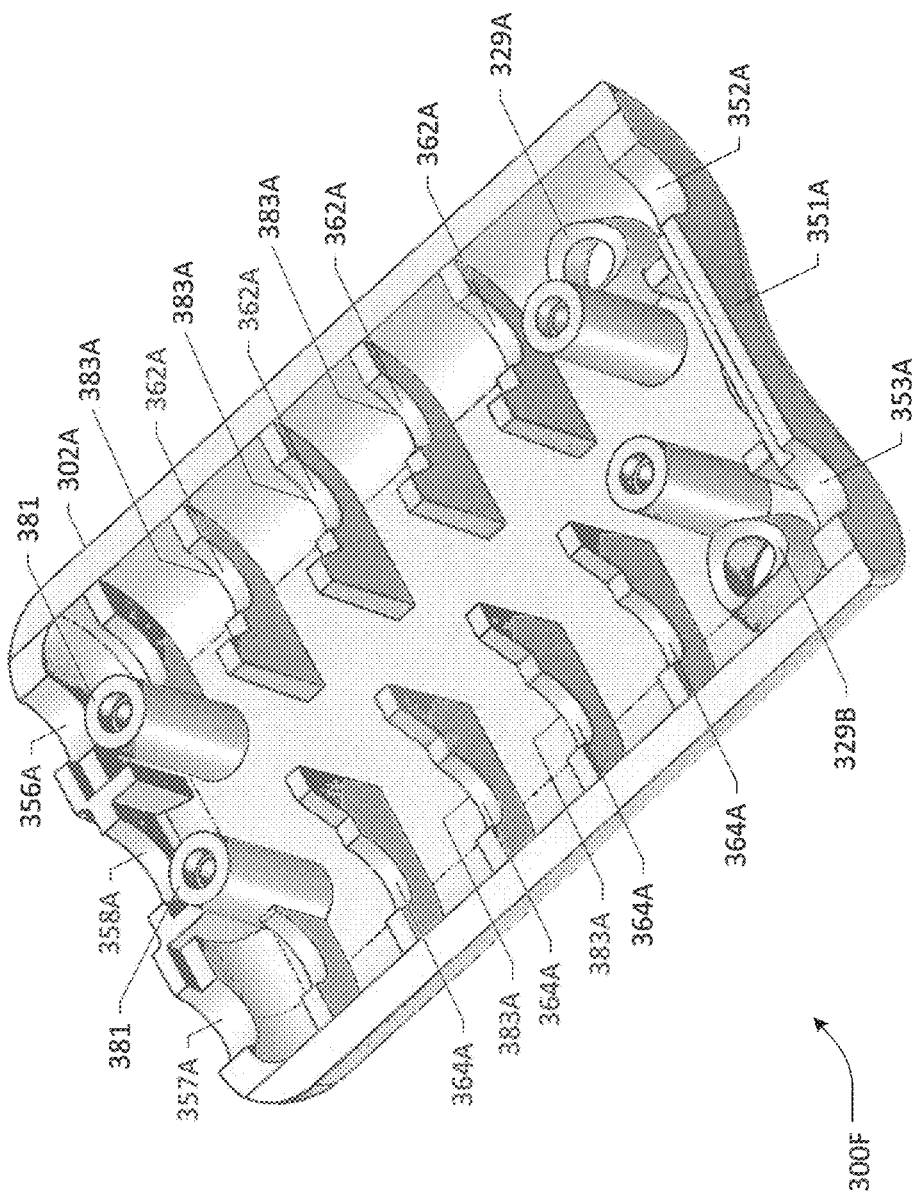
Figure 3G:
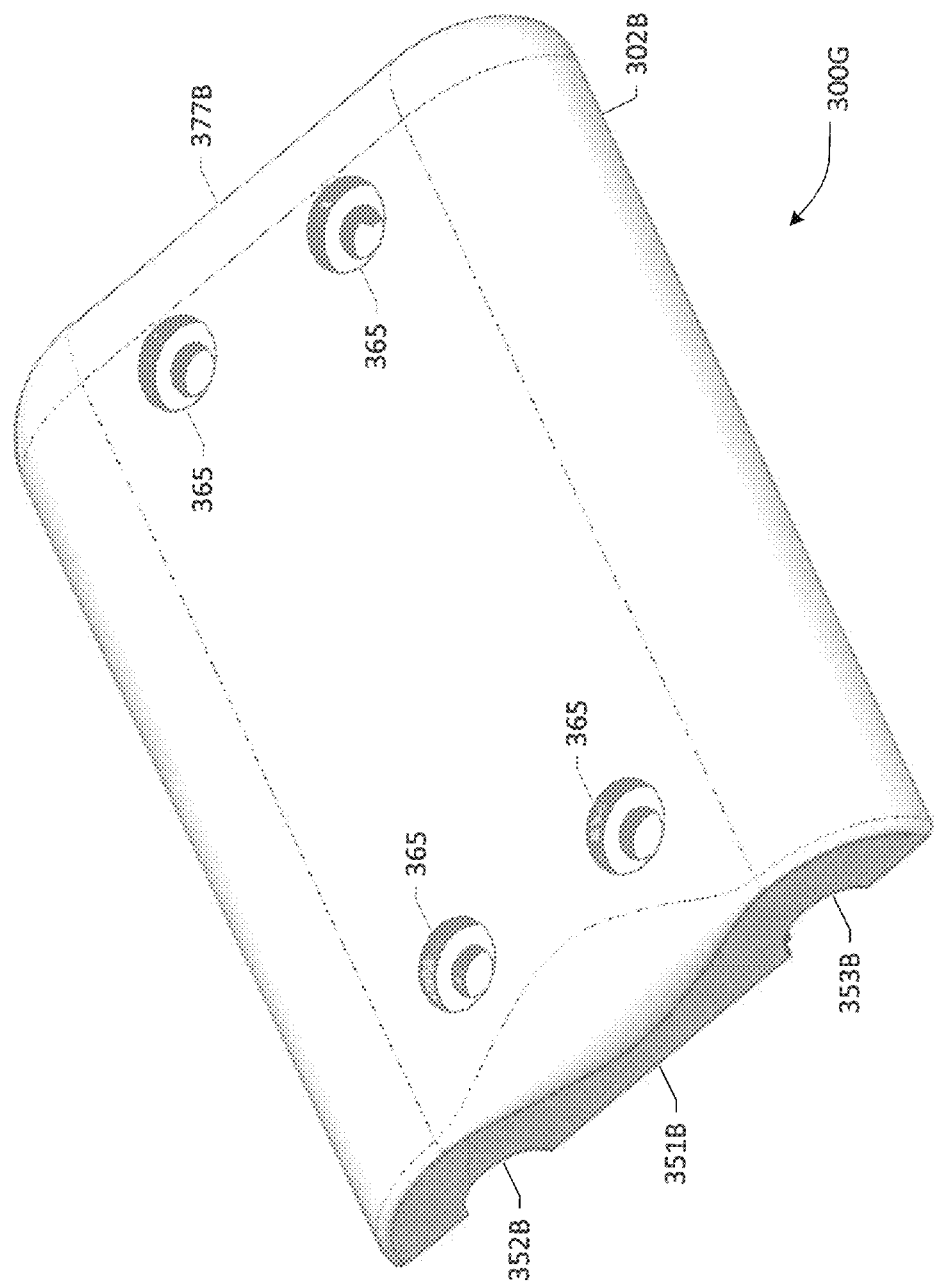
FIGS. 3G and 3H respectively depict exterior and interior views of a 3-dimensional perspective view of a bottom or lower housing portion of the example dual-lead connector shown in FIG. 3A.
Figure 3H:
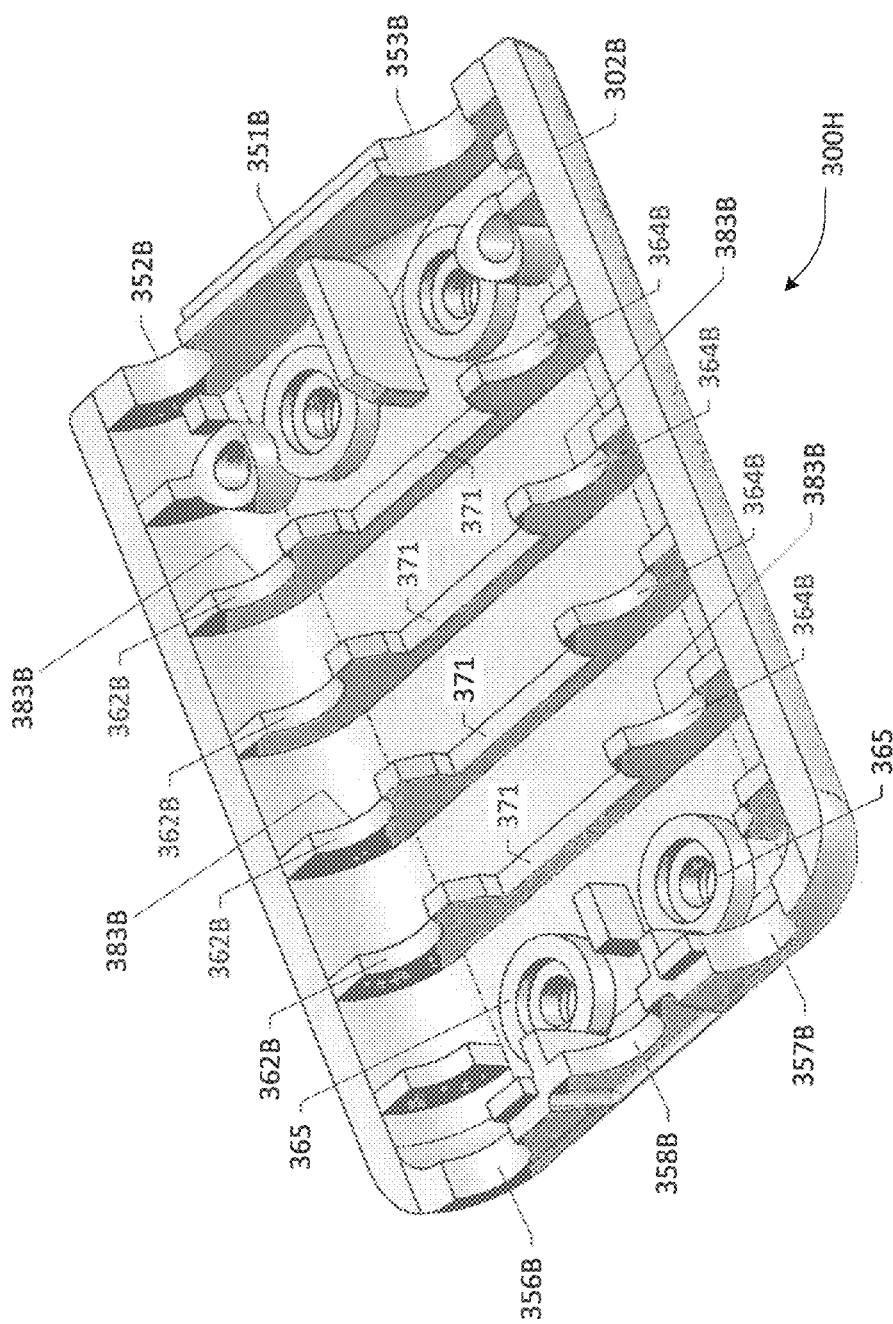

FIGS. 3E and 3F respectively depict exterior and interior views 300E, 300F of a 3-dimensional perspective view of upper housing portion 302A of the example dual-lead connector 300A shown in FIG. 3A. In similar fashion, FIGS. 3G and 3H respectively depict exterior and interior views 300G, 300H of a 3-dimensional perspective view of lower housing portion 302B of the example dual-lead connector 300A shown in FIG. 3A. Exterior view 300E of upper housing portion or casing 302A illustrates two view ports 329A, 329B, for facilitating visual indication or confirmation of full and proper insertion of a respective stimulation lead's proximal end having an indication band of suitable dimension as previously described. Where two or more insertion bands are provided at a stimulation lead's proximal end, a corresponding number of view ports may be configured in the upper housing portion 302A although such an arrangement may increase fabrication complexity and manufacturing cost. Because two cam lock assemblies 312A, 312B are to be housed in the dual-lead connector 300A, lead-side wall portion 351A of the upper housing portion 302A is provided with a pair of cutouts 352A, 353A, each having a suitable dimension (e.g., semi-circular or some other shape), which may form respective apertures for accommodating proximal ends of the cam lock assemblies 312A, 312B (i.e., near or adjacent to the cam knobs 314A, 314B) when the upper housing portion 302A is mated with the lower housing portion 302B that includes a corresponding lead-side wall portion 351B with matching pair of cutouts 352B, 353B, shown in FIGS. 3G and 3H. Likewise, a cable-side wall portion 377A of the upper housing portion 302A is provided with a pair of cutouts 356A, 357A, each having a suitable dimension (e.g., semi-circular or some other shape), which may form respective apertures for accommodating distal ends of the cam lock assemblies 312A, 312B (i.e., near or adjacent to the cam shaft termini) when the upper housing portion 302A is mated with the lower housing portion 302B that includes a corresponding lead-side wall portion 377B with matching pair of cutouts 356B, 357B, shown in FIG. 3H. Furthermore, the cable-side wall portions 377A/377B of the upper and lower housing portions 302A/302B may each be provided with a cutout 358A/358B of suitable dimensions to form an aperture for accommodating cable 326 that emerges from the cable-side wall 377A/377B for coupling with an external device, e.g., EPG 102.

As shown in FIG. 3F, the upper housing portion 302A may include appropriate receptacles, posts, recesses, etc., generally exemplified by posts 381, that may be configured to receive suitable coupling members such as, e.g., screws, bolts, rivets, binder posts, etc. for rigidly coupling to the lower housing portion 302B, which in turn may include appropriate holes, orifices or counter-sunk holes, etc, generally shown as apertures 365 (exemplified in FIGS. 3G and 3H) for presenting the coupling members. Further, each of the upper and lower housing portions 302A/302B may be provided with respective interior structural supporting members that may be contoured with cutouts to define longitudinal cavities or spaces to accommodate respective cam lock assemblies 312A/312B as noted previously. By way of illustration, the upper housing portion 302A is provided with two rows of upper plurality of ribs or transverse members 362A and 364A, wherein at least a subset of the transverse members each define a cutout 383A (shown in FIG. 3F). Likewise, the lower housing portion 302B is provided with corresponding lower plurality of ribs or transverse members 362B and 364B, wherein at least a subset of the transverse members each define a cutout 383B (shown in FIG. 3G). In one arrangement, each pair of the lower transverse members 362B and 364B may be coupled together via a corresponding transverse expansion member 371 or integrally formed to include the transverse expansion member 371, which together define a platform of spaced slats (e.g., slats 331 shown in FIG. 3A) upon which a PCB substrate, e.g., substrate 318, may be positioned.

Turning to FIGS. 4A-4D, depicted therein are several views that illustrate various steps of operating an example dual-lead connector 402 with respect to inserting and securing a trial stimulation lead according to an embodiment of the present disclosure. One skilled in the art will readily recognize that dual-lead connector 402 is an assembled version of the dual-lead connector 300A shown in FIG. 3A described hereinabove. Accordingly, it will be apparent that the foregoing description of FIGS. 3A-3H is equally applicable to FIGS. 4A-4D in pertinent parts, mutatis mutandis. Broadly, view 400A shown in FIG. 4A illustrates the step of inserting the stylet guide wire 308 into longitudinal guide wire slot 404 formed along a lateral side 406 of the dual-lead connector 402, wherein the stylet guide wire 308 is already at least partly pushed into the proximal end 306B of the stimulation lead 304B thereby leaving exposed at least a portion proximate to the stylet handle 310B. As noted previously, cam lock assembly 312B that is assembled in the dual-lead connector 402 with its cam knob 314B being visible (adjacent to the lead-side wall of the dual-lead connector 402) may be set in an unlocked position by rotating cam knob 314B in order to align its longitudinal channel 337 and associated longitudinal slit 349 with the guide wire slot 404. The exposed portion of guide wire 308 may then be inserted or pushed into the longitudinal channel 337, e.g., by a lateral sliding motion 405, via the aligned guide wire slot 404 and longitudinal slit 349. Once the guide wire 308 is inside the longitudinal channel 337, the proximal end 306B of the trial stimulation lead 304B may be pushed or otherwise guided into the cam lock assembly 312A through the cam knob orifice 345, e.g., by a longitudinal movement 407 toward the stylet's handle 310B, as illustrated in views 400B/400C of FIGS. 4B/4C. After completely pushing the proximal end 306B into the longitudinal channel 337 of cam lock assembly 312B (e.g., until the proximal end 306B buts up against the narrow diameter portion 341 of the longitudinal channel 337 and/or by obtaining visual confirmation of sighting the proximal end's insertion band 319 via view port 329B), cam knob 314B is rotated in a locking direction as shown in view 400D of FIG. 4D (e.g., counter-clockwise direction 409 by a quarter turn) to securely engage the proximal end 306B and present the terminal contact electrodes 317 to corresponding conductive spring contacts housed in the dual-lead connector 402.

Figure 5B:
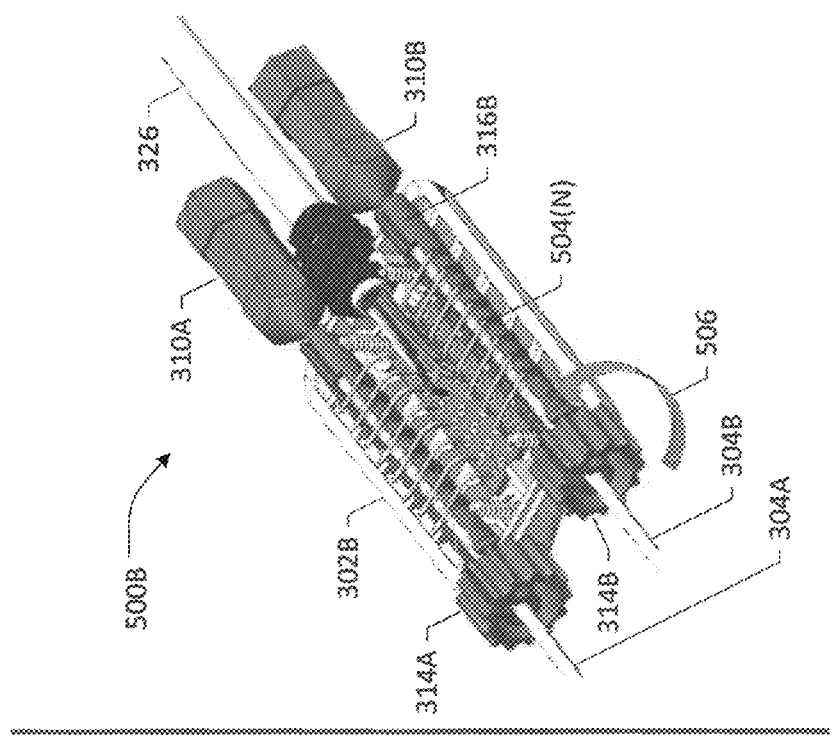
FIGS. 5A and 5B depict partial cutaway views of an example dual-lead connector for illustrating internal operations of a cam lock assembly in locking and unlocking conditions.
Figure 5A:
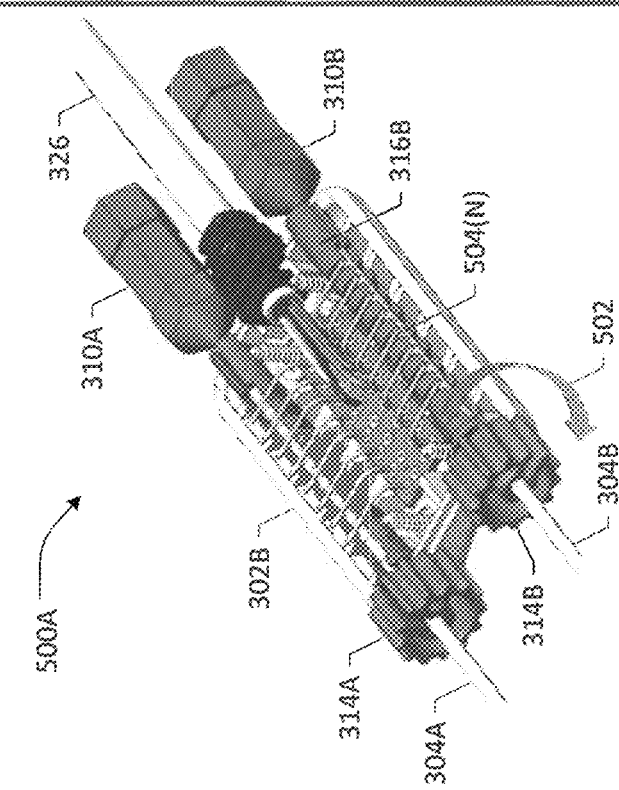

FIGS. 5A and 5B depict partial cutaway views of the example dual-lead connector 402 that illustrate internal operations of cam lock assembly 312B in locking and unlocking conditions. As exemplified in view 500A of FIG. 5A, a clockwise rotation 502 of cam knob 314B may be effectuated in aligning the longitudinal channel 337 and associated longitudinal slit 349 with the guide wire slot 404 (i.e., unlocked state), wherein a plurality of conductive spring contacts 504(N) are rested on the electrically inert cam shaft 316B (e.g., in between the ridges 343 formed on the cam shaft's exterior surface, if and where provided). In a locked state shown in view 500B of FIG. 5B, cam knob 314B is rotated in a counter-clockwise turn 506, thereby exposing terminal contact electrodes 317(N) of the proximal end 306B to the conductive spring contacts 504(N) for making secure electrical contact.

Figure 6A:
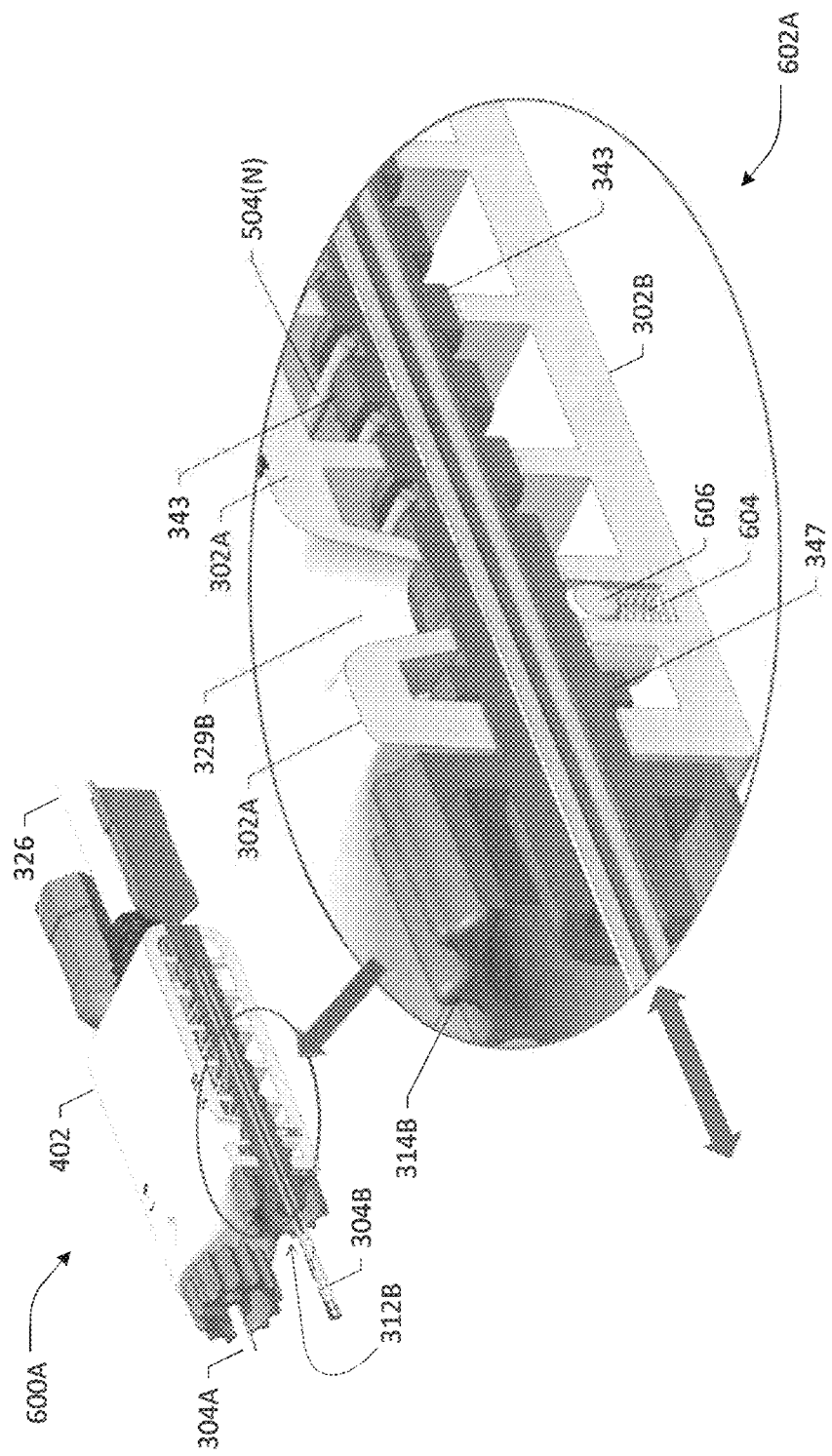
FIG. 6A depicts a partial cutaway view of the example dual-lead connector for illustrating additional details of a cam lock assembly in an unlocked position.
Figure 6B:
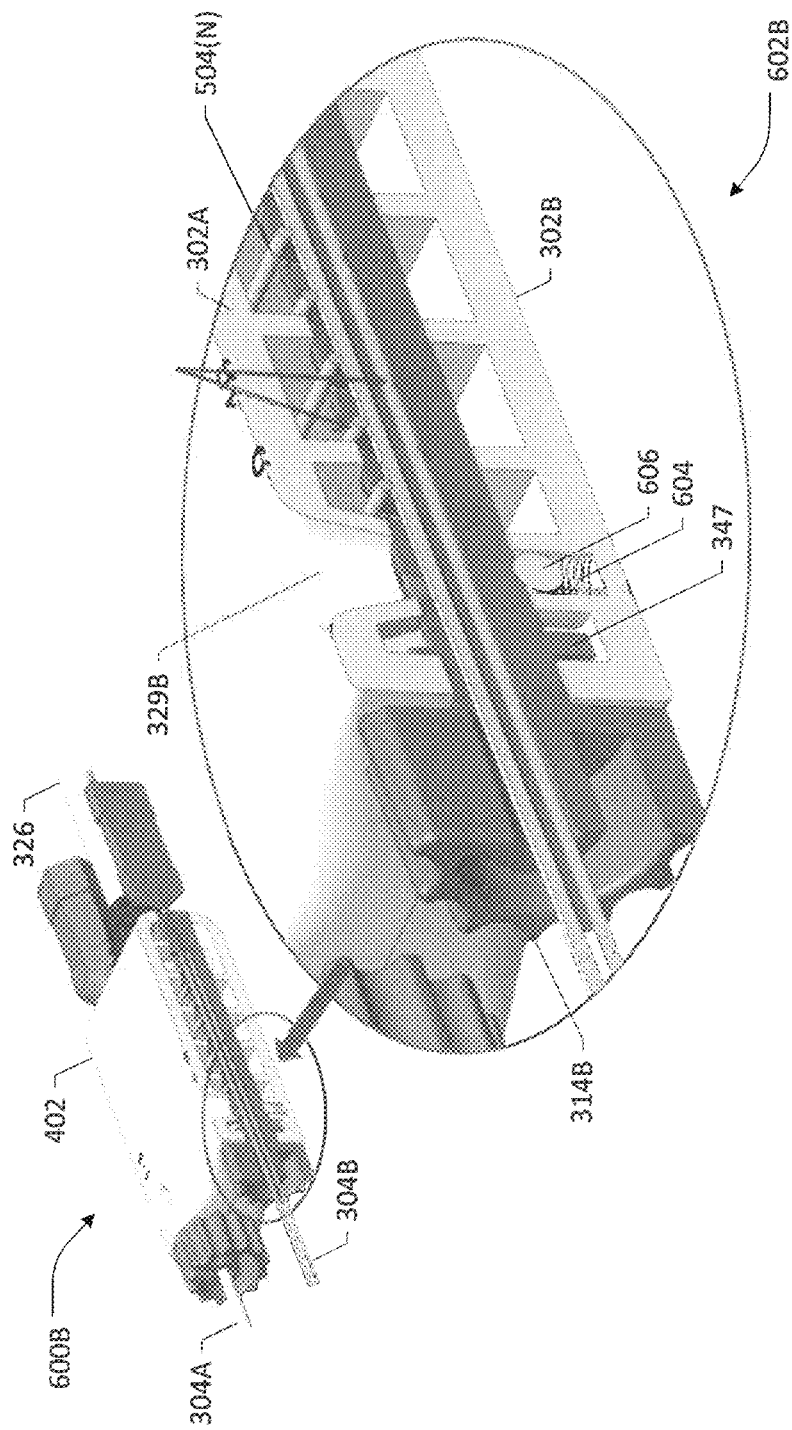
FIG. 6B depicts a partial cutaway view of the example dual-lead connector for illustrating additional details in a locked position of a cam lock assembly in a locked position.

FIGS. 6A and 6B depict partial cutaway views for illustrating additional details in unlocked and locked states of a cam lock assembly in the example dual-lead connector 402 set forth above. View 600A shown in FIG. 6A illustrates an overall partial cutaway view of the example dual-lead connector 402 along a longitudinal section through cam lock assembly 312B with the stimulation lead 304B inserted therein in an unlocked position. A close-up detail view 602A thereof illustrates the positioning of the conductive spring contacts 504(N) between ridges 343 on cam shaft 316A. In one variation, a spring-and-ball plunger having a ball 606 attached to spring 604 may be rigidly disposed in a recess of the lower housing portion 302B such that it may be disengaged or engaged depending on whether the cam lock assembly 312B is in unlocked or locked state. Further, it can be seen that projection tab 347 (configured to restrict the rotational movement of cam lock assembly 312A to a specified angular position, e.g., a quarter turn or 90 degrees as previously mentioned) is at least partially turned away from a retaining member of the lower housing portion 302B.

Partial cutaway view 600B shown in FIG. 6B illustrates in a close-up detail view 602B that highlights the foregoing mechanical features in a locked state of the cam lock assembly 312B. Because of the quarter-turn rotational movement, the longitudinal channel and associated slit of the cam lock assembly 312B now open "upward" (i.e., vertically facing up to the upper housing portion 302A) instead of opening sideways (i.e., to the longitudinal lateral side of the dual-lead connector 402), whereupon the terminal contact electrodes 317(N) become exposed to the conductive spring contacts 504(N), which bear down on the terminal contact electrodes 317(N) with appropriate tension. It will be apparent to skilled artisans that contact spring force can be adjusted to accommodate required lead pull out force constraints depending on the particular TSS/ETE application. Likewise, where a ball plunger mechanism 604/606 is provided, a combination of such mechanisms and the cantilever spring contacts 504(N) may also be adjusted to achieve appropriate lead pull out mechanical properties. Moreover, the ball plunger mechanism 604/606 may also be configured to provide a tactile feedback to an operator as to whether the proximal end of a stimulation lead is securely engaged when the cam lock assembly 312A is rotated into locked position, wherein the rotational movement may be suitably restricted by engagement of the projection tab 347 against the retaining member of lower housing portion 302B.

One skilled in the art will readily recognize that numerous variations, modifications and alterations, etc., may be implemented with respect to any combinations and/or sub-combinations of the foregoing features while ensuring that applicable mechanical design constraints are met in a multi-lead connector embodiment provided according to the teachings herein.

FIGS. 7A and 7B depict 3-dimensional perspective views of a quad-lead connector 702 using four cam lock assemblies operative to connect four trial stimulation leads 708-1 to 708-4 according to an embodiment of the present disclosure. View 700A shown in FIG. 7A is a top or front perspective view of the quad-lead connector 702 whereas view 700B shown in FIG. 7B illustrates a bottom or back perspective view of the quad-lead connector 702. It will be appreciated that apart from general form factor considerations, the operating principle of each of the cam lock assemblies securely housed in the example quad-lead connector 702 is essentially the same as the operating principle of cam lock assemblies 312A/312B described hereinabove in detail. Accordingly, the overall description of the cam lock assemblies 312A/312B will be equally applicable to the quad-lead connector embodiment 700 shown in FIGS. 7A and 7B, mutatis mutandis, as noted previously. Skilled artisans will recognize, however, that because of the necessary form factor requirements and/or concomitant design constraints, a quad-lead connector embodiment or other multi-lead connector embodiments may involve providing a plurality of guide wire slots corresponding to the cam lock assemblies (and, relatedly, the number of stimulation leads being connected) on suitable surface(s) of a 3-dimensional housing of the example multi-lead connector embodiment. Likewise, such form factor requirements may also necessitate positioning an egress compartment for appropriately routing an EPG-interfacing cable containing all the wiring to the EPG with respect to the four or multiple stimulation leads. For instance, if there are M stimulation leads to be connected and each stimulation has N electrodes, at least a total number of M×N conductors may need to be routed, groomed and encapsulated in an example EPG-interfacing cable. By way illustration, cable 714 having a suitable interface connector 716 is exemplified with respect to the quad-lead connector embodiment 702 shown in FIGS. 7A/7B, wherein a lateral edge or spine 712 of connector housing 705 is operative as an example cable egress compartment for facilitating a lateral side passage of the cable 714. As noted previously, cable 714 and interface connector 716 may be implemented in a variety of form factors and electrical configurations.

In one example arrangement, a plurality of guide wire slots 704-1 to 704-4 corresponding to the cam lock assemblies may be provided in a top or front surface 703A of the connector housing 705, preferably in a coplanar manner. It will be realized that the example quad-lead connector embodiment 702 is shown with four corresponding stylets or delivery tools in place, with the corresponding leads 708-1 to 708-4 (encasing respective guide wires) disposed in the respective cam lock assemblies, wherein respective stylet handles 710-1 to 710-4 are disposed on a vertical sidewall of the connector housing 705 orthogonal to the front surface 703A containing coplanar guide wire slots 704-1 to 704-4. Respective cam knobs 706-1 to 706-4 are disposed between the top and bottom surfaces 703A/703B of the connector housing 705, which not only facilitate easy rotational movement by using the operator's thumb and index finger in a "pinching" action but also provide a low profile form factor that can advantageously help reduce mechanical snagging of the housing 705, risk of detachment of the leads 706-1 to 706-4, and the like.

Figure 8:
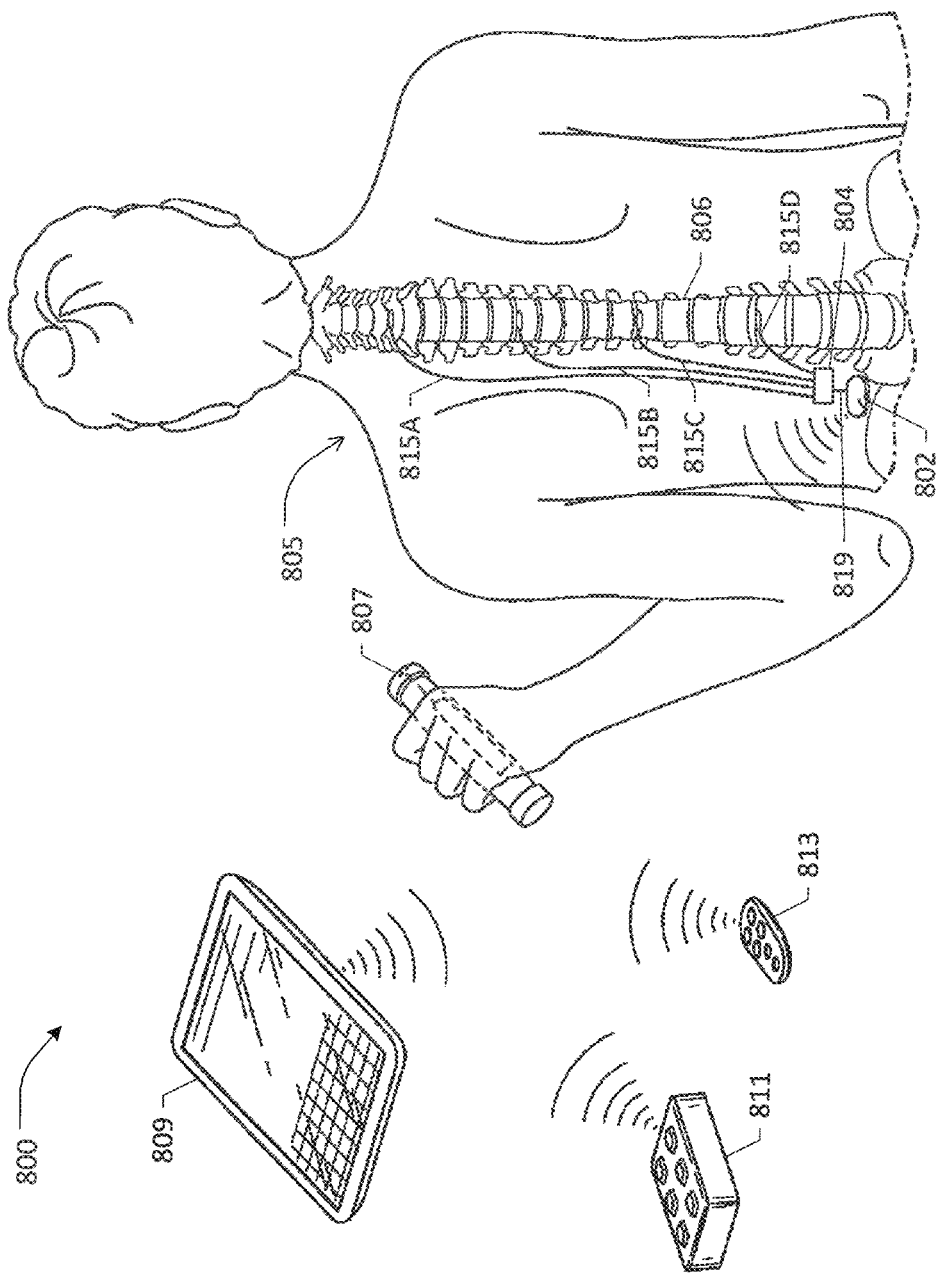
FIG. 8 depicts an example trial stimulation system using a wearable external pulse generator in combination with an embodiment of a multi-lead connector according to the teachings of the present disclosure.

FIG. 8 depicts an example trial SCS system 800 using a wearable EPG 802 in combination with an embodiment of a multi-lead connector 804 according to the teachings of the present disclosure. As illustrated in FIG. 8, wearable EPG 802 may be worn by a patient 805 around the patient's waist, preferably within a close proximity to the multi-lead connector 804, and coupled thereto via a short or long cable 819, in order to effectuate connectivity with respect to a plurality of trial stimulation leads 815A-D. As noted previously, wearable EPG 802 may also be worn in a number of configurations, either on the patient's body or in an article of clothing, with the multi-lead connector 804 suitably interfaced accordingly. Although multiple stimulation leads 815A-D are shown as extending to different parts of the patient's spinal cord 806, potentially involving multiple incisions, it should be appreciated that they may be implanted via a single incision into the spine's epidural space as well. A plurality of external devices such as tablet 809, smartphone 811, handheld PDA 813, or wand 807, etc., may be configured to communicate with EPG 802 via wired or wireless means. One skilled in the art will recognize that authorized medical or health professionals as well as the patient may monitor and/or modify various factors and protocols relating to the applied stimulation therapy during a trial period, for example, to assess a number of conditions, including but not limited to the incidence of technical and post-surgical complications such as lead migration, lead breakage, loose connection, battery failure, infection, leakage of cerebrospinal fluid, hematoma, undesirable stimulation, rapid or undesirable accumulation of residual voltages on the implanted electrodes, skin erosion, allergic reactions, etc., as well as conditions relating to the patient's general wellbeing, loss of the ability to perform daily activities, and how effective the stimulation therapy is in managing pain, etc.

Based on the foregoing Detailed Description, skilled artisans will recognize that embodiments of the present patent disclosure advantageously provide a low profile multi-lead connector system that is particularly beneficial in TSS/ETE applications involving multiple leads. Example embodiments also lend themselves to low cost manufacturing processes, thereby leading to lower overall product cost.

It will be further appreciated upon reference hereto that although dual-lead and quad-lead connector embodiments have been exemplified herein, other multiple-lead connector arrangements may also be practiced using a plurality of cam lock assemblies according to the teachings of the present disclosure. Further, such cam lock assemblies may be housed in a number of connector form factors, each with varying internal structural/support members that may be used for defining cavities configured to accommodate the cam lock assemblies in various arrangements. Moreover, any number, type or configuration of stimulation leads (e.g., percutaneous leads, paddle leads, etc.) may be used in association with an embodiment of the present patent disclosure within the scope of the teachings herein.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A stimulation therapy lead connector configured to facilitate electrical and mechanical connectivity between at least one stimulation lead and an external pulse generator, the at least one stimulation lead having a distal end with a plurality of stimulation electrodes and a proximal end with a corresponding plurality of terminal contact electrodes, the proximal end having an outer diameter and an inner diameter, wherein the distal end of the at least one stimulation lead is implantable in a patient using a guide wire inserted into the at least one stimulation lead from the proximal end to guide the distal end to a target tissue area, the stimulation therapy lead connector comprising:
   a housing;
   at least one cam lock assembly at least partially enclosed in the housing, the at least one cam lock assembly comprising a cam knob rigidly coupled to a cam shaft, the cam knob and the cam shaft having a longitudinal channel along a common axis, the longitudinal channel having at least a portion with a diameter sized to accommodate the outer diameter of the proximal end;
   a plurality of cantilevered conductive spring contacts mounted to a substrate securely disposed in the housing adjacent to the at least one cam lock assembly, the cantilevered conductive spring contacts operative to make electrical contact with the plurality of terminal contact electrodes of the proximal end after the proximal end is guided into the longitudinal channel using the guide wire inserted through a guide wire slot in the housing that is aligned with a longitudinal slit along the longitudinal channel when the cam knob is turned in a first direction and the at least one cam lock assembly is locked in a position by turning the cam knob in a second direction opposite to the first direction such that the longitudinal slit of the longitudinal channel is no longer aligned with the guide wire slot in the housing; and
   a plurality of conductors electrically connected to the plurality of cantilevered conductive spring contacts, the plurality of conductors encased in a cable having an interface for mating with an interface receptacle of the external pulse generator.

2. The stimulation therapy lead connector as recited in claim 1, wherein the longitudinal channel of the at least one cam lock assembly spans from a first orifice in the cam knob to a second orifice at a terminus of the cam shaft, the first orifice having a diameter substantially identical to the diameter of the longitudinal channel to allow passage of the proximal end when the at least one stimulation lead is inserted through the first orifice, the second orifice at the terminus of the cam shaft having a diameter sized to accommodate passage of the guide wire but not the proximal end when the proximal end is guided and fully inserted into the longitudinal channel of the at least one cam lock assembly.

3. The stimulation therapy lead connector as recited in claim 2, wherein the plurality of cantilevered conductive spring contacts are pivotally mounted to the substrate comprising a printed circuit board, the plurality of cantilevered conductive spring contacts configured to exert a tension on the plurality of terminal contact electrodes of the proximal end after the proximal end is guided into the longitudinal channel and the at least one cam lock assembly is locked, and further wherein the plurality of conductors are electrically connected to the plurality of cantilevered conductive spring contacts via corresponding conductive traces disposed on the printed circuit board.

4. The stimulation therapy lead connector as recited in claim 3, wherein an exterior surface of the cam shaft is provided with a projection tab operative to restrict a rotational movement of the cam knob around the common axis to only a quarter turn from a first position when the at least one cam lock assembly is unlocked and the longitudinal slit along the longitudinal channel is aligned to the guide wire slot in the housing to a second position when the at least one cam lock assembly is locked such that the longitudinal slit of the longitudinal channel is no longer aligned with the guide wire slot in the housing.

5. The stimulation therapy lead connector as recited in claim 3, wherein the at least one cam lock assembly comprises a plurality of cam lock assemblies, each configured to connect to a corresponding stimulation lead in a multi-lead configuration, and further wherein the housing includes a corresponding plurality of guide wire slots that are configured to align with respective longitudinal slits of corresponding cam lock assemblies when the corresponding cam lock assemblies are in an unlocked position.

6. The stimulation therapy lead connector as recited in claim 5, wherein the plurality of cam lock assemblies comprise two cam lock assemblies, each configured to connect to a corresponding stimulation lead in a dual-lead configuration, and further wherein the housing comprises an upper housing portion and a lower housing portion that are rigidly coupled to each other to form the housing that includes two guide wire slots formed on two lateral sides of the housing.

7. The stimulation therapy lead connector as recited in claim 6, wherein the cam knobs of the two cam lock assemblies are externally disposed outside the housing, the cam knobs each having a groove that forms at least a portion of the longitudinal slit of the corresponding cam lock assembly, the cam knobs disposed against a lead-side wall of the housing formed from coupling of the upper and lower housing portions.

8. The stimulation therapy lead connector as recited in claim 7, wherein the housing has a substantially rectangular 3-dimensional form, with a cable-side wall of the housing formed from coupling of the upper and lower housing portions substantially parallel to the lead-side wall of the housing, the cable-side wall having an aperture for allowing passage of the cable to interface with the external pulse generator.

9. The stimulation therapy lead connector as recited in claim 8, wherein the upper housing portion has a pair of apertures toward the lead-side wall of the housing, each aligned with the common axis of a respective cam lock assembly, each aperture positioned to line up with a location of an insertion band provided adjacent to the plurality of terminal contact electrodes of the proximal end of the corresponding stimulation lead such that when the cam knob of a respective cam lock assembly is turned to a locking position with the proximal end fully inserted into the longitudinal channel of the respective cam lock assembly, the aperture is operative to provide a visual indication of the insertion band to indicate full insertion of the proximal end into the longitudinal channel of the respective cam lock assembly.

10. The stimulation therapy lead connector as recited in claim 5, wherein the plurality of cam lock assemblies comprise four cam lock assemblies, each configured to connect to a corresponding stimulation lead in a quad-lead configuration, and further wherein the housing is formed to have four guide wire slots on a top portion of the housing that are aligned with respective longitudinal slits of corresponding cam lock assemblies in an unlocked position.

11. The stimulation therapy lead connector as recited in claim 10, wherein the cam knobs of the four cam lock assemblies are at least partially internally disposed with respect to the housing, the cam knobs each having a groove that forms at least a portion of the longitudinal slit of the corresponding cam lock assembly.

12. The stimulation therapy lead connector as recited in claim 10, wherein the housing has a substantially rectangular 3-dimensional form, with a cable egress compartment forming a lateral edge of the housing that is configured to facilitate a lateral side passage of the cable to interface with the external pulse generator.

13. The stimulation therapy lead connector as recited in claim 5, wherein the multiple stimulation leads each have a same number of terminal contact electrodes at respective proximal ends.

14. The stimulation therapy lead connector as recited in claim 5, wherein the multiple stimulation leads have a different number of terminal contact electrodes at respective proximal ends.

15. A trial stimulation therapy system operative to provide stimulation therapy to a patient for a trial period, the trial stimulation therapy system comprising:
    an external pulse generator configured to provide stimulation therapy via a plurality of trial stimulation leads implanted into the patient at one or more target tissue areas; and
    a multi-lead stimulation lead connector interfaced with the external pulse generator via a cable and configured to facilitate electrical and mechanical connectivity between the plurality of trial stimulation leads and the external pulse generator, the multi-lead stimulation lead connector comprising:
        a housing;
        a plurality of cam lock assemblies at least partially enclosed in the housing, each cam lock assembly configured to connect to a corresponding trial stimulation lead, wherein each cam lock assembly comprises a cam shaft rigidly fixed to a cam knob that is rotationally turnable around a common axis of the cam lock assembly to a first position to unlock the cam lock assembly for facilitating insertion of a proximal end of the corresponding trial stimulation lead into a longitudinal channel defined in the cam shaft and to a second position to lock the cam lock assembly for presenting a plurality of terminal contact electrodes to a corresponding conductive spring contacts disposed in the housing; and
        a plurality of conductors electrically coupled to the plurality of conductive spring contacts, wherein the plurality of conductors are at least partially encased in the cable and extend to an interface operative for mating with an interface receptacle of the external pulse generator, and wherein the conductive spring contacts comprise cantilevered conductive members pivotally mounted to a printed circuit board securely disposed in the housing adjacent to a corresponding cam lock assembly.

16. The trial stimulation therapy system as recited in claim 15, wherein the plurality of conductors are electrically connected to the corresponding cantilevered conductive members via conductive traces disposed in the printed circuit board.

17. The trial stimulation therapy system as recited in claim 16, wherein the housing is provided with a plurality of guide wire slots corresponding to the plurality of cam lock assemblies, each guide wire slot aligned to a longitudinal slot formed along the longitudinal channel of the corresponding cam lock assembly in an unlocked position.

18. The trial stimulation therapy system as recited in claim 17, wherein the cam knob of the corresponding cam housing is rotationally turned by a quarter turn to lock the corresponding cam lock assembly such that the longitudinal slit is no longer aligned with the corresponding guide wire slot of the housing.

\* \* \* \* \*